United States Patent
Mullen et al.

(10) Patent No.: US 12,290,337 B2
(45) Date of Patent: May 6, 2025

(54) PAYMENT CARDS AND DEVICES OPERABLE TO RECEIVE POINT-OF-SALE ACTIONS BEFORE POINT-OF-SALE AND FORWARD ACTIONS AT POINT-OF-SALE

(75) Inventors: Jeffrey David Mullen, Pittsburgh, PA (US); Bruce Cloutier, Pittsburgh, PA (US)

(73) Assignee: Dynamics Inc., Cheswick, PA (US)

( * ) Notice: Subject to any disclaimer, the term of this patent is extended or adjusted under 35 U.S.C. 154(b) by 0 days.

(21) Appl. No.: 12/339,054

(22) Filed: Dec. 19, 2008

(65) Prior Publication Data

US 2009/0159699 A1    Jun. 25, 2009

Related U.S. Application Data

(60) Provisional application No. 61/120,813, filed on Dec. 8, 2008, provisional application No. 61/119,366, filed
(Continued)

(51) Int. Cl.
*A61B 5/02* (2006.01)
*G06F 3/0488* (2022.01)
(Continued)

(52) U.S. Cl.
CPC ............ *A61B 5/02042* (2013.01); *A61B 5/02* (2013.01); *G06F 3/0488* (2013.01);
(Continued)

(58) Field of Classification Search
CPC ............ G07F 7/1008; G06K 19/06187; G06K 19/06206; G06K 19/10; G06K 7/10336;
(Continued)

(56) References Cited

U.S. PATENT DOCUMENTS 3,938,091 A   2/1976   Atalla et al.
4,094,462 A   6/1978   Moschner
(Continued)

FOREIGN PATENT DOCUMENTS

EP   0203683   12/1986
GB   2208458   3/1989
(Continued)

OTHER PUBLICATIONS

The Bank Credit Card Business. Second Edition, American Bankers Association, Washington, D.C., 1996.
(Continued)

*Primary Examiner* — Thien M Le
*Assistant Examiner* — Tae W Kim
(74) *Attorney, Agent, or Firm* — Morris Law Group; Robert W. Morris

(57) ABSTRACT

A payment card or other device (e.g., mobile telephone) is provided with a magnetic emulator operable to communicate data to a magnetic stripe read-head. A user can utilize buttons located on the card to perform activities that would otherwise be performed at an ATM, payment card reader, or by a waitress. A user can provide instructions on a card to accelerate a transaction. The information a user enters can be communicated to a point-of-sale device. For example, a user can enter into his/her card that the user desires $100 withdrawal from a checking account. The user can also enter his/her PIN into the card. The user can swipe his/her card into an ATM and instantly be provided with the desired $100.

29 Claims, 20 Drawing Sheets

Related U.S. Application Data on Dec. 2, 2008, provisional application No. 61/117,186, filed on Nov. 23, 2008, provisional application No. 61/112,766, filed on Nov. 9, 2008, provisional application No. 61/097,401, filed on Sep. 16, 2008, provisional application No. 61/090,423, filed on Aug. 20, 2008, provisional application No. 61/086,239, filed on Aug. 5, 2008, provisional application No. 61/081,003, filed on Jul. 15, 2008, provisional application No. 61/027,807, filed on Feb. 11, 2008, provisional application No. 61/026,846, filed on Feb. 7, 2008, provisional application No. 61/016,491, filed on Dec. 24, 2007.

(51) Int. Cl.

| | | |
|---|---|---|
| *G06K 7/00* | (2006.01) | |
| *G06K 7/08* | (2006.01) | |
| *G06K 7/10* | (2006.01) | |
| *G06K 19/06* | (2006.01) | |
| *G06K 19/07* | (2006.01) | |
| *G06K 19/073* | (2006.01) | |
| *G06K 19/077* | (2006.01) | |
| *G06K 19/08* | (2006.01) | |
| *G06Q 20/18* | (2012.01) | |
| *G06Q 20/20* | (2012.01) | |
| *G06Q 20/34* | (2012.01) | |
| *G06Q 20/38* | (2012.01) | |
| *G06Q 20/40* | (2012.01) | |
| *G06Q 30/0207* | (2023.01) | |
| *G06Q 30/0241* | (2023.01) | |
| *G06Q 30/0601* | (2023.01) | |
| *G06T 7/62* | (2017.01) | |
| *G06V 10/24* | (2022.01) | |
| *G06V 10/25* | (2022.01) | |
| *G07F 7/08* | (2006.01) | |
| *G07F 7/10* | (2006.01) | |

(52) U.S. Cl.
CPC .......... *G06K 7/0004* (2013.01); *G06K 7/084* (2013.01); *G06K 7/087* (2013.01); *G06K 7/10297* (2013.01); *G06K 19/06187* (2013.01); *G06K 19/06206* (2013.01); *G06K 19/07* (2013.01); *G06K 19/0702* (2013.01); *G06K 19/0704* (2013.01); *G06K 19/0723* (2013.01); *G06K 19/0725* (2013.01); *G06K 19/07345* (2013.01); *G06K 19/07703* (2013.01); *G06K 19/07705* (2013.01); *G06K 19/07707* (2013.01); *G06K 19/07709* (2013.01); *G06K 19/07749* (2013.01); *G06K 19/0775* (2013.01); *G06K 19/07766* (2013.01); *G06K 19/07769* (2013.01); *G06K 19/07773* (2013.01); *G06K 19/083* (2013.01); *G06Q 20/18* (2013.01); *G06Q 20/20* (2013.01); *G06Q 20/34* (2013.01); *G06Q 20/341* (2013.01); *G06Q 20/3415* (2013.01); *G06Q 20/352* (2013.01); *G06Q 20/385* (2013.01); *G06Q 20/401* (2013.01); *G06Q 30/0222* (2013.01); *G06Q 30/0241* (2013.01); *G06Q 30/0277* (2013.01); *G06Q 30/0641* (2013.01); *G06T 7/62* (2017.01); *G06V 10/24* (2022.01); *G06V 10/25* (2022.01); *G07F 7/0806* (2013.01); *G07F 7/1008* (2013.01); *G06T 2207/10024* (2013.01); *G06T 2207/30004* (2013.01); *G06V 2201/03* (2022.01)

(58) Field of Classification Search
CPC ............ G06Q 20/341; G06Q 20/3415; G06Q 20/40145; H04K 3/41; H04K 3/62; H04K 3/86
USPC ........................................................ 235/493
See application file for complete search history.

(56) References Cited

U.S. PATENT DOCUMENTS

| | | | |
|---|---|---|---|
| 4,353,064 A | 10/1982 | Stamm | |
| 4,394,654 A | 7/1983 | Hofmann-Cerfontaine | |
| 4,614,861 A | 9/1986 | Pavlov et al. | |
| 4,667,087 A | 5/1987 | Quintana | |
| 4,701,601 A * | 10/1987 | Francini et al. | 235/449 |
| 4,720,860 A | 1/1988 | Weiss | |
| 4,786,791 A | 11/1988 | Hodama | |
| 4,791,283 A | 12/1988 | Burkhardt | |
| 4,797,542 A | 1/1989 | Hara | |
| 4,806,745 A * | 2/1989 | Oogita | G06K 19/07 235/492 |
| 4,868,376 A | 9/1989 | Lessin et al. | |
| 4,959,788 A * | 9/1990 | Nagata | G06K 19/07 235/379 |
| 5,038,251 A | 8/1991 | Sugiyama et al. | |
| 5,168,520 A | 12/1992 | Weiss | |
| 5,237,614 A | 8/1993 | Weiss | |
| 5,276,311 A | 1/1994 | Hennige | |
| 5,347,580 A | 9/1994 | Molva et al. | |
| 5,361,062 A | 11/1994 | Weiss et al. | |
| 5,412,199 A | 5/1995 | Finkelstein et al. | |
| 5,434,398 A | 7/1995 | Goldberg | |
| 5,434,405 A | 7/1995 | Finkelstein et al. | |
| 5,478,994 A | 12/1995 | Rahman | |
| 5,479,512 A | 12/1995 | Weiss | |
| 5,484,997 A | 1/1996 | Haynes | |
| 5,485,519 A | 1/1996 | Weiss | |
| 5,585,787 A | 12/1996 | Wallerstein | |
| 5,591,949 A | 1/1997 | Bernstein | |
| 5,608,203 A | 3/1997 | Finkelstein et al. | |
| 5,623,552 A | 4/1997 | Lane | |
| 5,657,388 A | 8/1997 | Weiss | |
| 5,721,908 A | 2/1998 | Lagarde et al. | |
| 5,748,737 A | 5/1998 | Daggar | |
| 5,834,747 A | 11/1998 | Cooper | |
| 5,834,756 A | 11/1998 | Gutman et al. | |
| 5,856,661 A | 1/1999 | Finkelstein et al. | |
| 5,864,623 A | 1/1999 | Messina et al. | |
| 5,907,142 A | 5/1999 | Kelsey | |
| 5,907,350 A | 5/1999 | Nemirofsky | |
| 5,913,203 A | 6/1999 | Wong et al. | |
| 5,937,394 A | 8/1999 | Wong et al. | |
| 5,955,021 A | 9/1999 | Tiffany, III | |
| 5,955,961 A * | 9/1999 | Wallerstein | 340/5.4 |
| 5,956,699 A | 9/1999 | Wong et al. | |
| 6,012,048 A * | 1/2000 | Gustin et al. | 705/39 |
| 6,025,054 A | 2/2000 | Tiffany, III | |
| 6,045,043 A | 4/2000 | Bashan et al. | |
| 6,076,163 A | 6/2000 | Hoffstein et al. | |
| 6,085,320 A | 7/2000 | Kaliski | |
| 6,095,416 A | 8/2000 | Grant et al. | |
| 6,118,490 A | 9/2000 | Moore et al. | |
| 6,130,621 A | 10/2000 | Weiss | |
| 6,145,079 A | 11/2000 | Mitty et al. | |
| 6,157,920 A | 12/2000 | Jakobsson et al. | |
| 6,161,181 A | 12/2000 | Haynes, III et al. | |
| 6,176,430 B1 | 1/2001 | Finkelstein et al. | |
| 6,182,894 B1 | 2/2001 | Hackett et al. | |
| 6,189,098 B1 | 2/2001 | Kaliski | |
| 6,199,052 B1 | 3/2001 | Mitty et al. | |
| 6,206,293 B1 | 3/2001 | Gutman et al. | |
| 6,240,184 B1 | 5/2001 | Huynh et al. | |
| 6,241,153 B1 | 6/2001 | Tiffany, III | |
| 6,256,873 B1 | 7/2001 | Tiffany, III | |
| 6,269,163 B1 | 7/2001 | Rivest et al. | |
| 6,286,022 B1 | 9/2001 | Kaliski et al. | |
| 6,286,710 B1 | 9/2001 | Paek | |

(56) References Cited

U.S. PATENT DOCUMENTS

| | | |
|---|---|---|
| 6,308,890 B1 | 10/2001 | Cooper |
| 6,313,724 B1 | 11/2001 | Osterweil |
| 6,389,442 B1 | 5/2002 | Yin et al. |
| 6,393,447 B1 | 5/2002 | Jakobsson et al. |
| 6,411,715 B1 | 6/2002 | Liskov et al. |
| 6,446,052 B1 | 9/2002 | Juels |
| 6,460,141 B1 | 10/2002 | Olden |
| 6,592,044 B1 | 7/2003 | Wong et al. |
| 6,607,127 B2 | 8/2003 | Wong |
| 6,609,654 B1 | 8/2003 | Anderson et al. |
| 6,631,849 B2 | 10/2003 | Blossom |
| 6,655,585 B2 | 12/2003 | Shinn |
| 6,681,988 B2 | 1/2004 | Stack et al. |
| 6,705,520 B1 | 3/2004 | Pitroda et al. |
| 6,755,341 B1 | 6/2004 | Wong et al. |
| 6,764,005 B2 | 7/2004 | Cooper |
| 6,769,607 B1 * | 8/2004 | Pitroda et al. ............... 235/380 |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,902,116 B2 | 6/2005 | Finkelstein |
| 6,970,070 B2 | 11/2005 | Juels et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,221 B1 | 5/2006 | Tumey et al. |
| 7,039,223 B2 | 5/2006 | Wong |
| 7,044,394 B2 | 5/2006 | Brown |
| 7,051,929 B2 | 5/2006 | Li |
| 7,083,094 B2 | 8/2006 | Cooper |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Routhenstein |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,334,732 B2 | 2/2008 | Cooper |
| 7,337,326 B2 | 2/2008 | Palmer et al. |
| 7,346,775 B2 | 3/2008 | Gasparini et al. |
| 7,356,696 B1 | 4/2008 | Jakobsson et al. |
| 7,357,312 B2 * | 4/2008 | Gangi ............... 235/380 |
| 7,357,319 B1 | 4/2008 | Lin et al. |
| 7,359,507 B2 | 4/2008 | Kaliski |
| 7,360,688 B1 | 4/2008 | Harris |
| 7,363,494 B2 | 4/2008 | Brainard et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,426 B2 | 9/2009 | Osterweil et al. |
| 7,591,427 B2 | 9/2009 | Osterweil |
| 7,599,192 B2 * | 10/2009 | Pennaz et al. ............... 361/761 |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,828,207 B2 | 11/2010 | Cooper |
| 7,840,975 B2 | 11/2010 | Matheny et al. |
| 2001/0034702 A1 | 10/2001 | Mockett et al. |
| 2001/0047335 A1 | 11/2001 | Arndt et al. |
| 2002/0043566 A1 | 4/2002 | Goodman et al. |
| 2002/0059114 A1 | 5/2002 | Cockrill et al. |
| 2002/0082989 A1 | 6/2002 | Fife et al. |
| 2002/0096570 A1 | 7/2002 | Wong et al. |
| 2002/0108066 A1 | 8/2002 | Masui |
| 2002/0120583 A1 | 8/2002 | Keresman, III et al. |
| 2002/0123967 A1 | 9/2002 | Wang |
| 2003/0004889 A1 * | 1/2003 | Fiala et al. ............... 705/64 |
| 2003/0034388 A1 | 2/2003 | Routhenstein et al. |
| 2003/0052168 A1 | 3/2003 | Wong |
| 2003/0057278 A1 * | 3/2003 | Wong ............... 235/451 |
| 2003/0116635 A1 | 6/2003 | Taban |
| 2003/0152253 A1 | 8/2003 | Wong |
| 2003/0163287 A1 * | 8/2003 | Vock et al. ............... 702/187 |
| 2003/0171096 A1 | 9/2003 | Ilan et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0226899 A1 | 12/2003 | Finkelstein |
| 2004/0035942 A1 * | 2/2004 | Silverman ............... 235/493 |
| 2004/0097054 A1 | 5/2004 | Abe |
| 2004/0127256 A1 | 7/2004 | Goldwaithe |
| 2004/0133787 A1 | 7/2004 | Doughty |
| 2004/0162732 A1 | 8/2004 | Rahim et al. |
| 2004/0172535 A1 | 9/2004 | Jakobsson |
| 2004/0177045 A1 | 9/2004 | Brown |
| 2004/0179718 A1 | 9/2004 | Chou |
| 2005/0043997 A1 | 2/2005 | Sohata et al. |
| 2005/0070327 A1 | 3/2005 | Watanabe |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0116026 A1 | 6/2005 | Burger et al. |
| 2005/0119940 A1 | 6/2005 | Concilio et al. |
| 2005/0154643 A1 | 7/2005 | Doan et al. |
| 2005/0228959 A1 | 10/2005 | D'Albore et al. |
| 2005/0269401 A1 | 12/2005 | Spitzer et al. |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0086806 A1 * | 4/2006 | Conraux et al. ............... 235/492 |
| 2006/0091223 A1 | 5/2006 | Zellner |
| 2006/0161435 A1 | 7/2006 | Atef et al. |
| 2006/0163353 A1 | 7/2006 | Moulette et al. |
| 2006/0174104 A1 | 8/2006 | Crichton et al. |
| 2006/0196931 A1 * | 9/2006 | Holtmanns et al. ............... 235/380 |
| 2006/0231611 A1 | 10/2006 | Chakiris |
| 2006/0256961 A1 | 11/2006 | Brainard et al. |
| 2006/0283958 A1 * | 12/2006 | Osterweil ........ G06K 19/06206 235/492 |
| 2006/0289632 A1 | 12/2006 | Walker |
| 2007/0034700 A1 * | 2/2007 | Poidomani ......... G06K 19/0702 235/492 |
| 2007/0063776 A1 | 3/2007 | Okuda |
| 2007/0114274 A1 | 5/2007 | Gibbs et al. |
| 2007/0124321 A1 | 5/2007 | Szydlo |
| 2007/0131759 A1 | 6/2007 | Cox et al. |
| 2007/0152070 A1 | 7/2007 | D'Albore |
| 2007/0152072 A1 | 7/2007 | Frallicciardi et al. |

(56) References Cited

U.S. PATENT DOCUMENTS

| | | |
|---|---|---|
| 2007/0153487 A1 | 7/2007 | Frallicciardi et al. |
| 2007/0174614 A1 | 7/2007 | Duane et al. |
| 2007/0176622 A1* | 8/2007 | Yamazaki .................. 324/770 |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0192249 A1 | 12/2007 | Biffle et al. |
| 2007/0285246 A1 | 12/2007 | Koyoma |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0096326 A1 | 4/2008 | Reed |
| 2008/0116285 A1* | 5/2008 | Shoemaker ...... G06K 19/06187 235/493 |
| 2008/0126398 A1 | 5/2008 | Cimino |
| 2008/0128515 A1 | 6/2008 | Di Iorio |
| 2008/0140536 A1 | 6/2008 | Ruiz |
| 2008/0148394 A1 | 6/2008 | Poidomani et al. |
| 2008/0201264 A1 | 8/2008 | Brown et al. |
| 2008/0209550 A1 | 8/2008 | Di Iorio |
| 2008/0288699 A1 | 11/2008 | Chichierchia |
| 2008/0294930 A1 | 11/2008 | Varone et al. |
| 2008/0302877 A1 | 12/2008 | Musella et al. |
| 2009/0013122 A1 | 1/2009 | Sepe et al. |
| 2009/0036147 A1 | 2/2009 | Romano |
| 2009/0037275 A1 | 2/2009 | Pollio |
| 2009/0046522 A1 | 2/2009 | Sepe et al. |
| 2009/0108064 A1 | 4/2009 | Fernandes et al. |
| 2009/0143104 A1 | 6/2009 | Loh |
| 2009/0150295 A1 | 6/2009 | Hatch et al. |
| 2009/0152365 A1 | 6/2009 | Li et al. |
| 2009/0159663 A1 | 6/2009 | Mullen |
| 2009/0159673 A1 | 6/2009 | Mullen |
| 2009/0159689 A1 | 6/2009 | Mullen |
| 2009/0170432 A1 | 7/2009 | Lortz |
| 2009/0191811 A1 | 7/2009 | Griffin |
| 2009/0210308 A1 | 8/2009 | Toomer |
| 2009/0222383 A1 | 9/2009 | Tato |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0288012 A1 | 11/2009 | Hertel |
| 2009/0290704 A1 | 11/2009 | Cimino |
| 2009/0303885 A1 | 12/2009 | Longo |
| 2010/0019033 A1 | 1/2010 | Jolivet |
| 2010/0023449 A1 | 1/2010 | Skowronek |
| 2010/0045627 A1 | 2/2010 | Kennedy |
| 2010/0066701 A1 | 3/2010 | Ningrat |
| 2010/0078472 A1 | 4/2010 | Lin et al. |
| 2010/0108771 A1 | 5/2010 | Wong |
| 2010/0153269 A1 | 6/2010 | McCabe |
| 2010/0230793 A1 | 9/2010 | Kudose |
| 2010/0304670 A1 | 12/2010 | Shuo |
| 2011/0028184 A1 | 2/2011 | Cooper |
| 2011/0066550 A1 | 3/2011 | Shank |

FOREIGN PATENT DOCUMENTS

| | | |
|---|---|---|
| GB | 2420098 | 5/2006 |
| JP | 05210770 A | 8/1993 |
| WO | WO9852735 | 11/1998 |
| WO | WO0247019 | 6/2002 |
| WO | WO06066322 | 6/2006 |
| WO | WO06080929 | 8/2006 |
| WO | WO06105092 | 10/2006 |
| WO | WO06116772 | 11/2006 |
| WO | WO07141779 | 12/2007 |
| WO | WO08064403 | 6/2008 |

OTHER PUBLICATIONS

A Day in the Life of a Flux Reversal. http://www.phrack.org/issues.html?issue=37&id=6#article. As viewed on Apr. 12, 2010.
Dynamic Virtual Credit Card Numbers. http://homes.cerias.purdue.edu/~jtli/paper/fc07.pdf. As viewed on Apr. 12, 2010.
USPTO, International Search Report, dated Apr. 28, 2009.
English translation of JP 05210770 A.
U.S. Appl. No. 60/594,300, Poidomani et al.
U.S. Appl. No. 60/675,388, Poidomani et al.
Extended European Search Report for European Patent Application No. 08865573.3, dated Jan. 26, 2012.
AU, Patent Examination Report No. 1, dated Oct. 11, 2012.
EPO, Article 94(3) Communication, dated Feb. 5, 2013.
Magnetic Stripe Card. http://en.wikipedia.org/w/index.php?title=Magnetic_stripe_card&oldid=174608901. Dated Nov. 29, 2007.
See EPO, Article 94(3) Communication, dated Feb. 5, 2013.
EPO, Rule 115(1) Summons to Oral Proceedings, Sep. 18, 2013.

* cited by examiner

400

PAYMENT CARDS AND DEVICES OPERABLE TO RECEIVE POINT-OF-SALE ACTIONS BEFORE POINT-OF-SALE AND FORWARD ACTIONS AT POINT-OF-SALE

CROSS-REFERENCE TO RELATED APPLICATIONS

This application claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

Payment card transactions are slow. A user may need to wait in line before performing actions on an ATM. A user may need to wait for a waitress to bring him/her a receipt before calculating a tip for a purchase. A user may need to wait for a cashier to prompt the user to perform actions at a card reader before the user can perform such actions. Such traditional systems are deficient as a user may spend a large amount of time at a payment card reader interacting with the payment card reader. It is therefore desirable to decrease the amount of time a user may need to interact with a payment card reader.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches or more) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

A read-head detector, or an array of read-head detectors, may be able to, for example, determine the type of reader that the card entered into. For example, a read-head detector array may determine, for example, when a motorized reader was utilized, an insertion reader was utilized, or a user-swipe reader was utilized. Such information may be stored and communicated to a remote storage device (e.g., a remote database). This stored information may be utilized to combat, for example, card cloning. For example, if a particular number of cards (e.g., 10 more) that made consecutive purchases from a machine (e.g., an ATM) detected more than one reader, then, for example, the system may make an autonomous determination that an illegal cloning device was located on front of that ATM machine. If, for example, multiple cards use a restaurant point-of-sale terminal and determine that multiple readers were used then, for example, a computer can make an autonomous determination that cloning may have occurred at the restaurant.

A material may be sandwiched between the two layers to assist in reducing the affect of the electromagnetic fields from one set of coil segments on the side of the material opposite that set of coil segments. Such an interior material may be insulated such that the material does not short the coil segments. Additionally, such an interior material may be chosen, for example, such that the material does not saturate when the coil is conducting current. The coil and material may run, for example, along the location of a track of magnetic data for a payment card. Accordingly, a coil may be fabricated so that the coil wraps around an interior material.

A material may be placed and/or printed on a PCB layer and sandwiched between two other PCB layers. These two other layers may each include coil segments and vias. The middle layer may also include vias such that the material is fabricated to be located in the center of the coil. The material may take a cylindrical, rectangular, square, or any type of shape. Four layers may also be utilized, where the coil segments are printed on a surface of the exterior layers and one or more materials are printed and/or placed on/between the interior layers. A material may be a magnetic material, ferromagnetic material, ferrimagnetic material, or any type of material. For example, copper may be printed on a PCB layer and plated with a material (e.g., nickel, iron, chrome, tin, gold, platinum, cobalt, zinc, alloys). A material, for example, may have a relative permeability multiple times greater than the permeability of a vacuum. A material, for example, may have a permeability of 2 to 25,000. A material may include, for example, a permalloy, iron, steel, ferrite, nickel or any other material. A material may be an alloy such as a nickel-iron alloy. Such a nickel-iron alloy may include, for example, nickel (e.g., 75-85%), iron, copper, molybdenum and may be placed through one or more annealing processes. Annealing may occur before and/or after the material is placed/printed on a layer of material (e.g., a PCB layer or other layer). A similar and/or different material may be placed either above and/or below a portion, or the entire, set of paths on a layer for a coil. Accordingly, a material may be placed in the interior of a coil as well as along a side of the coil.

Displays may be provided near user interfaces or other structures. For example, a display may be provided next to an LED. Cards may be programmed during manufacturing so that these displays may display particular information. Accordingly, for example, the same card architecture may be utilized to provide a number of different types of cards. A user may utilize user interfaces (e.g., mechanical or capacitive interfaces) to change the function of the display. For example, codes may be entered to reconfigure the displays. Alternatively, for example, a user may utilize buttons to select information to be displayed on displays associated with user interfaces. A code may associate a name of a store with a button and/or a dollar amount. For example, a display may be configured to read "Target $50." Information may be entered manually, but also may be received by a card. For example, a user may swipe a card a second time through a magnetic stripe reader and receive information via a magnetic emulator. This received information may be utilized to update information on the card (e.g., the balance of a gift card, credit account, and/or debit account). Information may also be received by an RFID antenna and/or IC chip located on a card and in communication with a central processor (or distributed processors). For example, transaction information (e.g., list of past transactions, stores where transactions occurred, amounts of transactions) and account information (e.g., balance information, bill information, amount due information) may be communicated to the card and displayed on one or more displays.

A dynamic card may be manufactured in a variety of ways. For example, a dynamic card may be printed onto a flexible material (e.g., a flexible polymer). Multiple layers of this material may be bonded together to form a multiple layer flexible structure. This multiple layer structure may be laminated (e.g., via hot, warm and/or cold lamination) to form a card. The card may be programmed before or after lamination. A card may be programmed via a direct connection between a programmer and one or more contacts on a card. A card may be programmed via a capacitive, optical, or inductive communication via a communication link between a programmer and one or more components (e.g., a contact) on a card. Accordingly, for example, a card may be laminated and capacitively, optically, or inductively programmed. After programming, a processor on the card may be signaled to burn-out its programming communication channel(s) such that no further programming may occur. A portion of the card may not be laminated. Accordingly, a programmer may connect to this non-laminated portion of the card. The non-laminated portion of the card may be laminated after programming. Alternatively, for example, the non-laminated portion of the card may be cut after programming (e.g., and after the processor burns-out its programming ports so the processor cannot be further programmed).

Additional external communication devices may be provided on a card. For example, a USB port or Wi-Fi antenna may be provided on a card. Such additional external communication devices may, for example, allow a user to communicate with stationary computer, laptop, or other device. Such communication devices may, for example, be utilized to load gift cards, or other information (e.g., transactional or account information) from a laptop to a card or other device. A card is provided that includes a light sensor such that information can be communicated to a card via light (e.g., via a light transmitted from a TV or website).

Information that is transmitted to a magnetic stripe readhead can be changed by a card. The information can be changed based on software that is pre-loaded into a card. Similarly, the information can be determined, at least in part, by a user of the card. Accordingly, a user of a card may enter information into a card via user interfaces in order to change at least part of the information transmitted through a magnetic-stripe reader, via a magnetic stripe read-head, to a remote payment card processing server.

A user may command a card to communicate particular information to obtain a variety of functionalities. For example, a user may be required to perform a variety of actions at a point-of-sale (POS) magnetic stripe reader. Such actions may require that user to spend a particular amount of time. Accordingly, such a user may perform these activities before reaching the POS device. The user's decisions may be communicated through a POS reader output device such as a magnetic emulator/encoder, RFID antenna, and/or IC chip. Accordingly, in doing so, a user may decrease the time the user spends at a POS device. Accordingly, the time it takes to complete a transaction at a POS device can be significantly reduced.

User interfaces, such as capacitive or mechanical buttons, may be included on a card. One or more buttons may be associated with one or more tip amounts. Accordingly, for example, a user may press a particular button and a corresponding percentage may be communicated to a POS reader. Accordingly, a remote server may complete a transaction for the full-amount of the purchase (e.g., total cost, tax, and tip). The remote server may also pre-authorize the transaction for this full-amount such that a user can, for example, easily change the tip if desired. In determining the amount of the tip on the payment card, a user may increase the speed of a transaction as the user may not have to perform any math himself/herself. The user may instead be presented with a receipt that notes the desired tip as well as the total amount that includes the tip. Such a total operation may be performed in numerous locations. For example, a POS reader may recognize the inclusion of tip information in an card output signal (e.g., an RFID, IC chip, and/or magnetic stripe signal).

The POS reader may then perform the associated functions. Alternatively, for example, software located on a cash-register (e.g., a restaurant's cash register) may receive the information from the POS reader and may notice that tip information was included in a card output signal. Accordingly, for example, a card may be branded with indicia corresponding to a particular restaurant chain (e.g., TGIF, Red Robin, or Applebee's) and software may be added to the POS readers and/or cash registers associated with that particular restaurant chain.

A remote server may receive payment information provided to a payment card reader by a payment. This information may include data fields (e.g., discretionary data fields). A remote server may recognize that the received payment information includes user-defined data such as, for example, tip information. Accordingly, the remote server may perform additional processing steps based on this user-defined data. For example, the remote server may determine a tip amount based on received tip information and may authorize a payment card transaction for the amount. The remote server may communicate information back to a POS device indicative of the determined tip amount and/or total authorized amount.

A card may include buttons indicative of particular tip amounts. Alternatively, a card may include numerical buttons and a button indicative of a tip. Accordingly, a user may determine any tip amount that can be defined by the numerical buttons. Furthermore, the numerical buttons may be utilized for executing functionality other than functionality that corresponds to determining and providing tips.

A card is provided in which a user can enter his/her Personal Identification Number (PIN) into the card using one or more user interfaces. This PIN may be communicated in an output signal from a card (e.g., a signal from an RFID antenna, IC Chip, or magnetic emulator/encoder). Accordingly, for example, a user can enter his/her PIN into a card while waiting in a line for an ATM machine. The user can communicate this PIN from the card to the ATM machine using a reader output device on the card. The ATM machine may, for example, recognize that a valid PIN was received from the card and may provide the user with a welcome screen instead of a screen requesting the entry of a PIN.

Similarly, PIN-based purchases may be made where a user enters his/her PIN on a card instead of enters his/her PIN on a POS device. Furthermore, a user may utilize an on-card PIN entry instead of, for example, an on-receipt signature. Accordingly, for example, a user may purchase a meal at a restaurant. A waitress may present the user with a check. A user may press a button associated to providing an on-card PIN. The user may also press a button associated to a particular tip percentage. Accordingly, for example, the waitress may take possession of the card and may swipe the card through his/her POS device. The PIN may be utilized in lieu of a signature such that the total (including tip) is immediately authorized). The waitress may then, for example, present a receipt to a user that confirms that a financial transaction was completed, that an on-card PIN-based authentication was utilized, and the total amount including a line item for a tip amount.

A system is provided in which a user may utilize a PIN entry instead of a signature to complete a signature-based transaction. The PIN may be, for example, passed-through from a card to a remote server using an output device (e.g., RFID antenna, IC chip, magnetic emulator/encoder). The server may recognize that a card desires utilizing an on-card PIN instead of a signature by looking at a particular character or characters of discretionary data. Furthermore, the server may recognize that a card is one that can perform an on-card PIN functionality by, for example, looking at a particular character or characters of transmitted information. For example, a server may determine that a card includes an on-card PIN functionality by, for example, looking at a number of digits of a user's payment card number (e.g., first six digits of a credit card number) and comparing this data to a corresponding list of partial payment card numbers that include an on-card functionality. Accordingly, if a card is determined to have an on-card PIN functionality (or any pre-POS functionality or other functionality) then the server may look at other characters of the received data (e.g., a particular discretionary data field) to determine the user's execution of the function. Data received by a server may, for example, include the PIN number that a user entered into a card. Alternatively, data received by the server may include information representative of the user entering in the correct PIN onto the card. Accordingly, for example, a card may receive a PIN and determine that the PIN is correct. The card may then send a particular character (e.g., a "1") in a particular discretionary data location to the remote server.

A card with pre-ATM functionality is provided in order to expedite the ATM process when a user is provided with the ability to physically interact with the ATM machine. Accordingly, a user may perform ATM activities on his/her card so that when the user physically interacts with an ATM machine, the time of the interaction is reduced. A card is provided with a button that allows a user to designate that the user desires to withdrawal a particular amount of cash from an ATM. Accordingly, for example, the user may enter in his/her PIN onto a card while waiting in a line to use a particular ATM. The user can also utilize the user interfaces of the card to denote that the user desires a particular amount (e.g., $100) of cash from a particular account of the user's (e.g., checking). Accordingly, a card may communicate this information to an ATM when a user swipes or inserts his/her card into the ATM. Accordingly, a user may be prompted with a confirmation screen to confirm the user's pre-ATM card actions. In doing so, a user may decrease the amount of time he/she spends at an ATM machine.

A user may also be provided with a button that corresponds to a user-defined set of actions. For example, such a button may be indicative of taking a particular amount of money out of a checking account while transferring a particular amount of money from a savings account to that checking account, and not requiring a receipt from the ATM. The user may, for example, determine the actions that are associated with this button through an online website for a particular bank or card issuer. Accordingly, for example, when a user presses the button and the information is communicated to a reader (e.g., at an ATM), the remote server may retrieve information indicative of the actions the users desired to perform when the button was pressed. Accordingly, for example, users may customize his/her card via a website.

Additionally, for example, a user may reprogram his/her card with new code on a website. For example, a user may select a particular set of actions for a particular button on a website and the website may direct the user to hold his/her card to a display screen of the user's computer. A portion of the display screen may then flash light to the card. The card may include light sensors to determine characteristics of the flashing light. In doing so, information may be communicated from a website to a card.

A card is provided in which a user can perform pre-cashier checkout activities on his/her card while waiting in a checkout line. For example, a user may enter his/her PIN into a card for a PIN-based card payment as well as select, utilizing one or more user interfaces on the card, a variety of checkout options such as a particular amount of desires cash-back. The user may also determine, for example, that the user does or does not desire a receipt and that the user desires to utilize a particular type of payment (e.g., a credit payment from a credit account). The user's desired decisions may be communicated to a cashier via a cash register connected to a payment card/device reader.

A card is provided that includes a user interface associated with determining whether a user desires a receipt for a particular transaction. In doing so, for example, the information associated with the user's decision on whether the user desires a receipt can be communicated through a payment card reader. In doing so, a cashier may, for example, not need to ask a user whether the user desires a receipt—thus decreasing the time of interaction between the user and the cashier.

Coupons can be loaded into cards in a variety of ways. For example, a user may utilize computer interfaces on a card in order to load a coupon. For example, a user may be provided with a code and may enter that code into his/her card. Coupons, or other information, may also be communicated to a card via a television commercial or show. For example, a commercial for a product may include flashing indicia in a corner of the commercial. A user may hold his/her card up to the corner of the commercial and the information (e.g., coupon) may be communicated to the card. For example, a card may encrypt information based on an encryption algorithm. If this integrity of the algorithm is compromised, a commercial can be provided on national or regional television such that information can be communicated to cards that would change the encryption algorithm the card uses to encrypt data the card provides to payment card readers.

A card is provided that includes buttons associated with items. For example, a card may include a button associated with a particular type of drink (e.g., cola) and/or a particular types of snack (e.g., potato chips). A user that is waiting in line at a vending machine may, for example, press the button on his/her card associated with a particular item that the user desires to purchase. Accordingly, a user may swipe his/her card through a payment card magnetic stripe reader and the vending machine may receive payment information in addition to item ordering information. Accordingly, the vending machine may receive the desired order information, execute the order (e.g., vend the user a bottle of cola), and complete a payment transaction based on the amount of the ordered item and the payment card information provided by the payment card to the vending machine.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which.

DETAILED DESCRIPTION OF THE INVENTION

Figure 1:
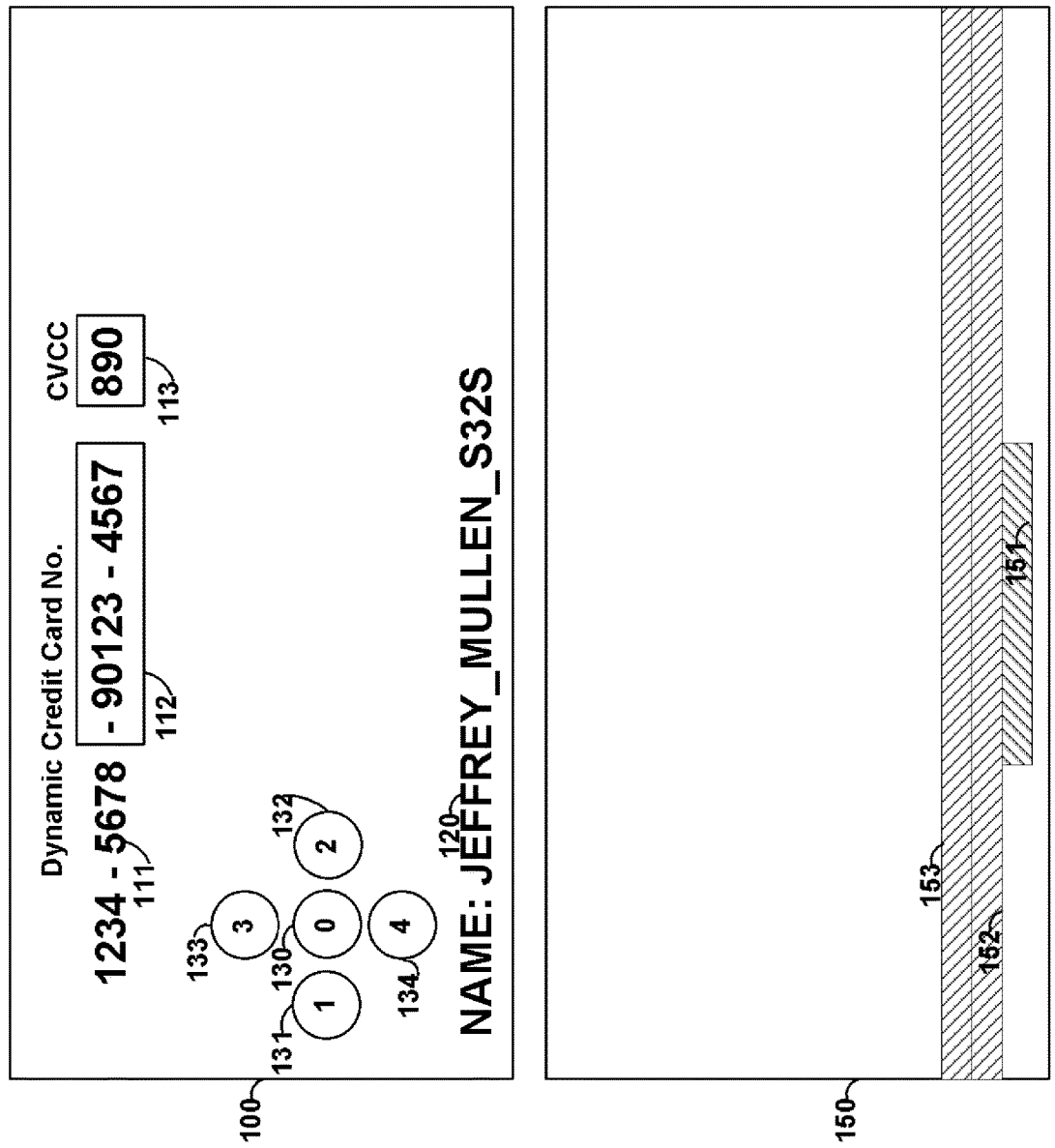
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card or any other type of card (e.g., security access or identification card). Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identified using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. Card 150 may be provided. Card 150 may include static magnetic stripe tracks 153 and 152. Magnetic emulator 151 may be included and may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 kHz.

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Emulator 151 may be included such that dynamic information may be communicated to a magnetic stripe reader, for example, without a magnetic stripe via an electromagnetic signal transmitted directly from emulator 151 to a read-head of a magnetic stripe reader. Any combination of emulators and static magnetic tracks may be utilized for a card or device (e.g., two magnetic emulators without any magnetic stripes).

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
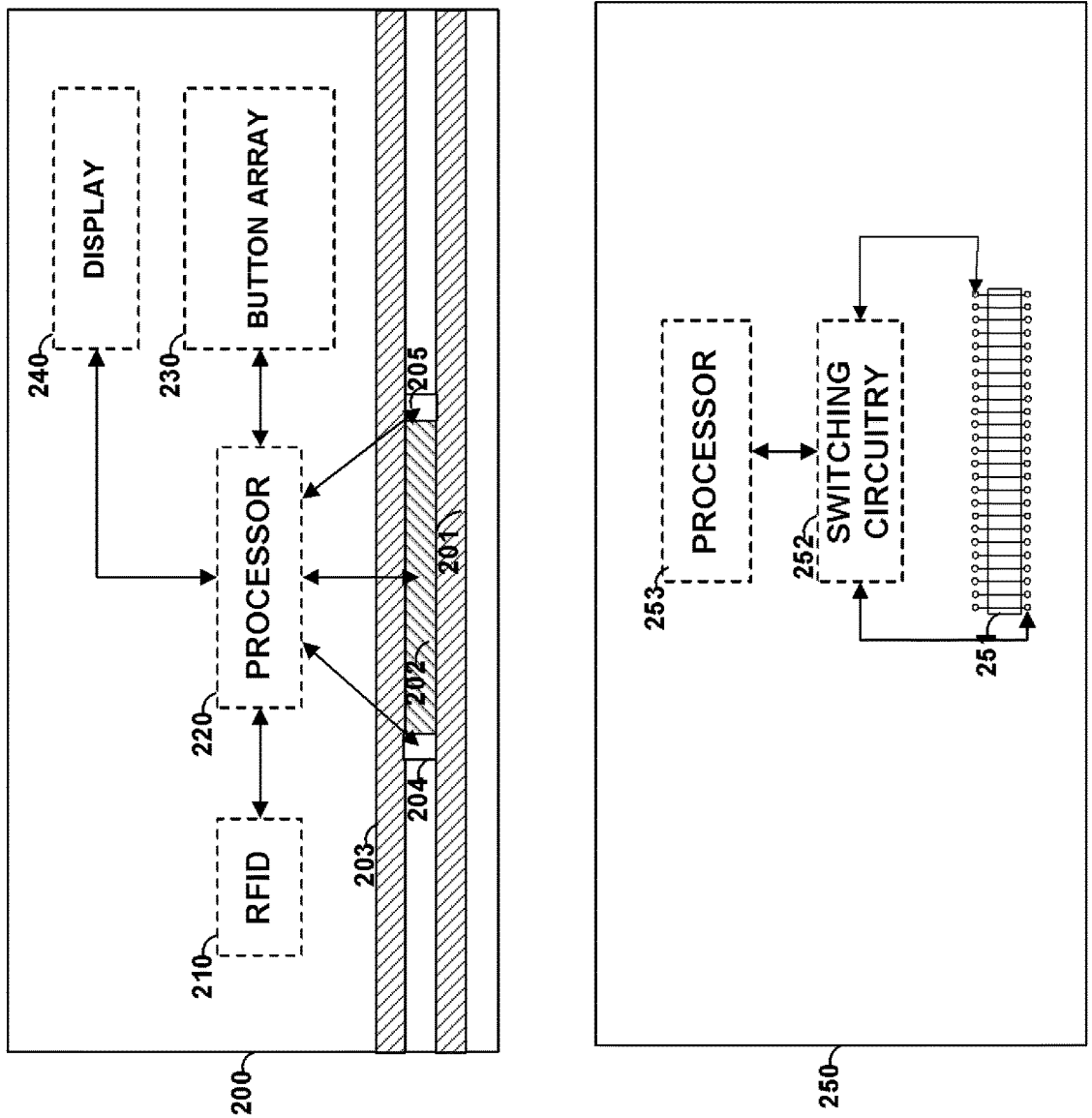
FIG. 2 is an illustration of cards and associated circuitry constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202. Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230. A smart-card chip may, for example, be included on card 200 in lieu of, or in addition to, RFID 210.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes a coil operable to communicate data serially to a magnetic stripe reader. Similarly, for example, emulator 251 may receive information for a magnetic stripe encoder. Persons skilled in the art will appreciate that a coil may run across the length of a card such that a read-head moves along the length of the coil and can receive information transmitted serially from the coil. The coil may extend into multiple tracks such that multiple read-heads receive information from the coil. Track information can be sent serially (e.g., track 1 information followed by track 2 information). Multiple coils may be driven separately and placed in different zones such that a single read-head moves from coil-to-coil (e.g., zone-to-zone) and power is conserves as only coils in a particular zone (or zones) may be utilized to communicate information any particular time. Separate coils may be utilized for separate tracks. Materials may be placed in the interior of each coil to assist with manipulating the electromagnetic field produced by the coils. Material may be placed above or below a coil to further manipulate the electromagnetic field produced by the coil. Switching circuitry 252 may include, for example, one or more transistors that may be utilized to control the direction of current via emulator 251 (e.g., the polarity of voltage(s) across a drive resistor). For example, a coil may be utilized to transmit a string of information to a particular read-head. Different coils may transmit information at different speeds (or at the same speed). Different coils may transmit different amounts of information. For example, three coils may be provided. The coil closest to the bottom of the long-end of a card may transmit at least 79 characters. The coil next closest to the bottom of the long-end of a card may transmit at least 40 characters of information. The coil next closest to the bottom of the long-end of the card may transmit at least 107 characters. One or more coils may have different character sets (e.g., a 6-bit character set or a 7-bit character set). The last bit in a character may include, for example, a parity bit. Additional synching information may be transmitted before and after the data information to assist with synching a magnetic stripe reader. For example, a string of zeros may be communicated before and after communicating primary data. Characters may be included in the data information for other purposes such as an LRC character.

Figure 3:
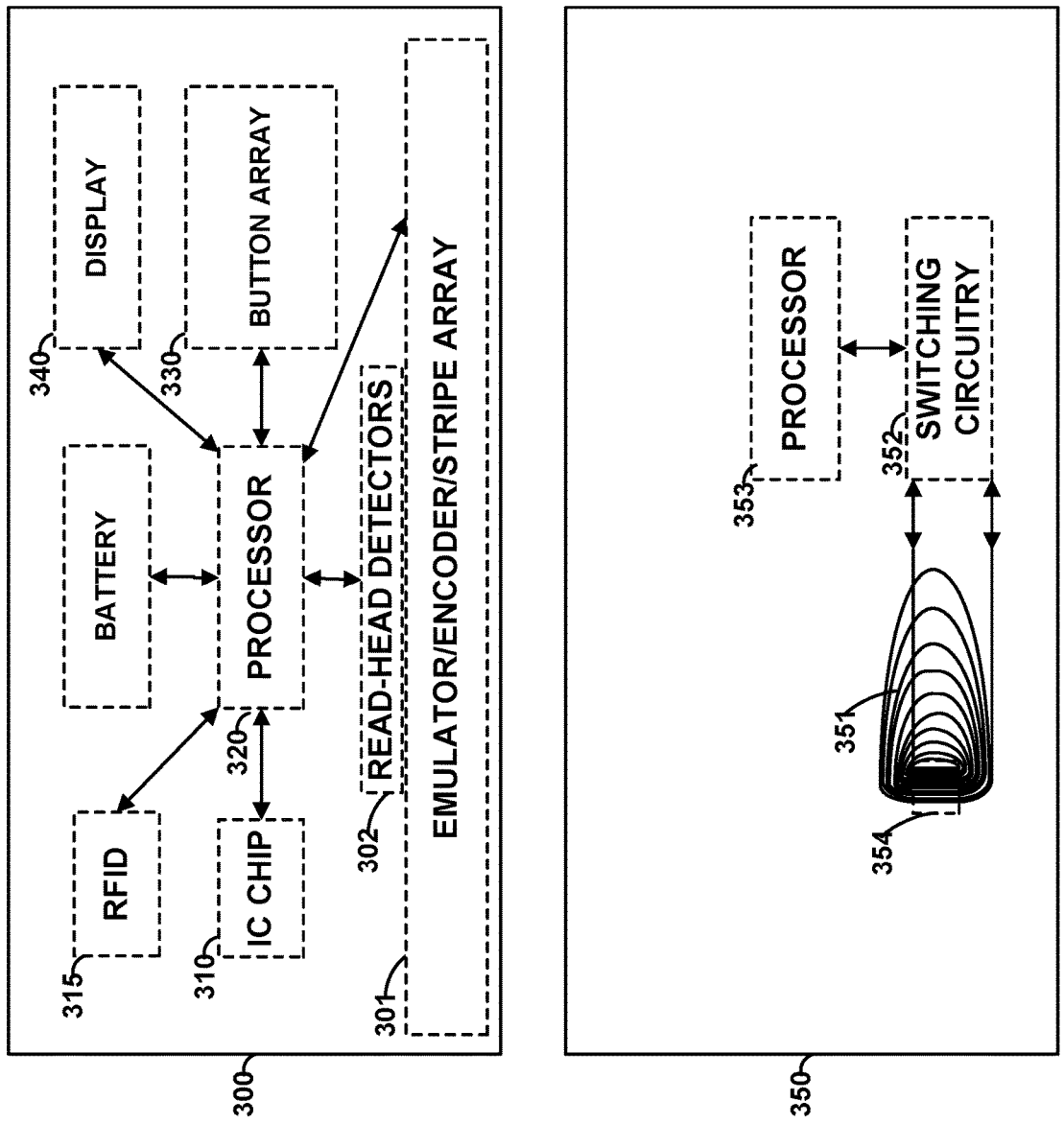
FIG. 3 is an illustration of cards constructed in accordance with the principles of the present invention.

FIG. 3 shows card 300 that may include a number of components. Card 300 may include one or more processors 320. A processor may include, for example, cache memory, RAM, and/or ROM. Additional memory may be provided on card 300. For example, additional non-volatile, volatile, cache memory, RAM, and/or ROM may be provided on card 300. Battery 325 may be provided on card 300. Battery 325 may be, for example, a lithium polymer battery and may have a thickness less than a millimeter (e.g., approximately 0.5 mm). RFID antenna 315 may be provided on card 300 and may communicate data to an RFID reader. Persons skilled in the art will appreciate that an RFID may be included that is a passive or active RFID. IC chip 310 may be included on card 300 and may communicate data to an IC chip reader. Device 301 may be included to communication information to a magnetic stripe reader. Device 301 may include any number of magnetic emulators, magnetic encoders that encode magnetic stripes, and/or magnetic stripes. For example, device 301 may include a magnetic emulator for one track of magnetic data and a magnetic stripe for a second track of data. Alternatively, for example, device 301 may include two emulators for separate tracks of data. An emulator may, for example, communicate information to a read-head of a magnetic stripe reader serially. One or more read-head detectors 302 may be provided to detect a read-head (or other attribute) of a magnetic stripe reader. Additional detectors may be included to detect, for example, when a card is provided into an IC chip reader and/or an electromagnetic field from an RFID reader. Button array 330 may be provided, for example, to receive input from a user. Button array 330 may include any number of buttons (e.g., 4, 5, 10, or more than 10). Button array 330 may include, for example, mechanical buttons, capacitive buttons, or any type of user interface. One or more displays 340 may also be included. A display may be, for example, an electronic ink display (e.g., electrochromic display), LCD display, or any other type of display. Display 340 may be flexible.

Display 340 may be printed onto a layer during a printed fabrication process (e.g., PCB). Additionally, for example, battery 325 may be printed onto a layer during a printed fabrication process (e.g., PCB). Similarly, a magnetic emulator may be printed onto a layer during a printed fabrication process (e.g., PCB). Other components may be printed onto a layer during a printed fabrication process (e.g., PCB) such as capacitive read-head detectors, and capacitive touch sensors. Accordingly, a display, battery, read-head detector, and button array may be printed on one or more layers that are bonded together and laminated.

FIG. 3 shows card 350 that may include, for example, processor 353, switching circuitry 352, and emulator 351 having active region 354. Switching circuitry 352 may, for example, control the direction of current through emulator 351 in order to change the direction of electromagnetic fields generated by emulator 351 such that data may be communicated serially to a magnetic stripe read-head. Persons skilled in the art will appreciate that emulator 351 may be fabricated on a single layer and that region 354 may include coil segments dense enough to generate an electromagnetic field that can be recognized by a read-head of a magnetic stripe reader.

Figure 4:
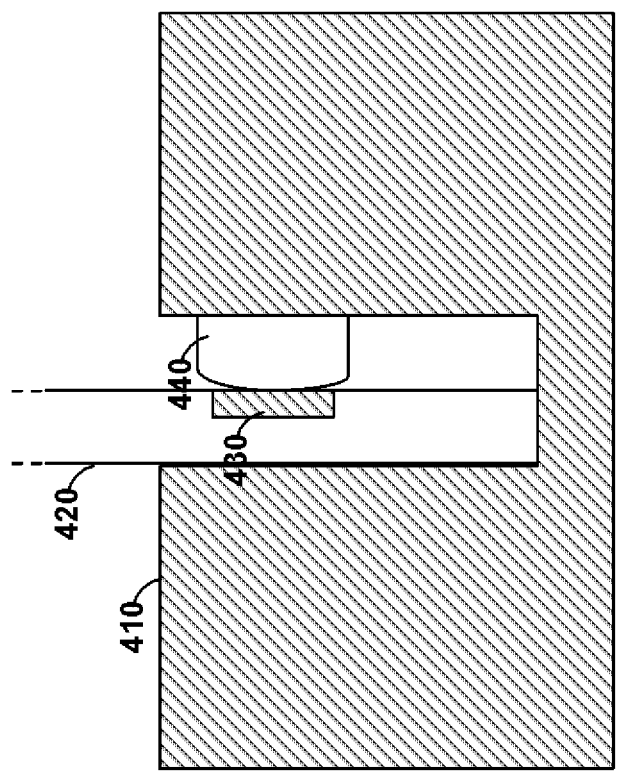
FIG. 4 is an illustration of a card located adjacent to a read-head of a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
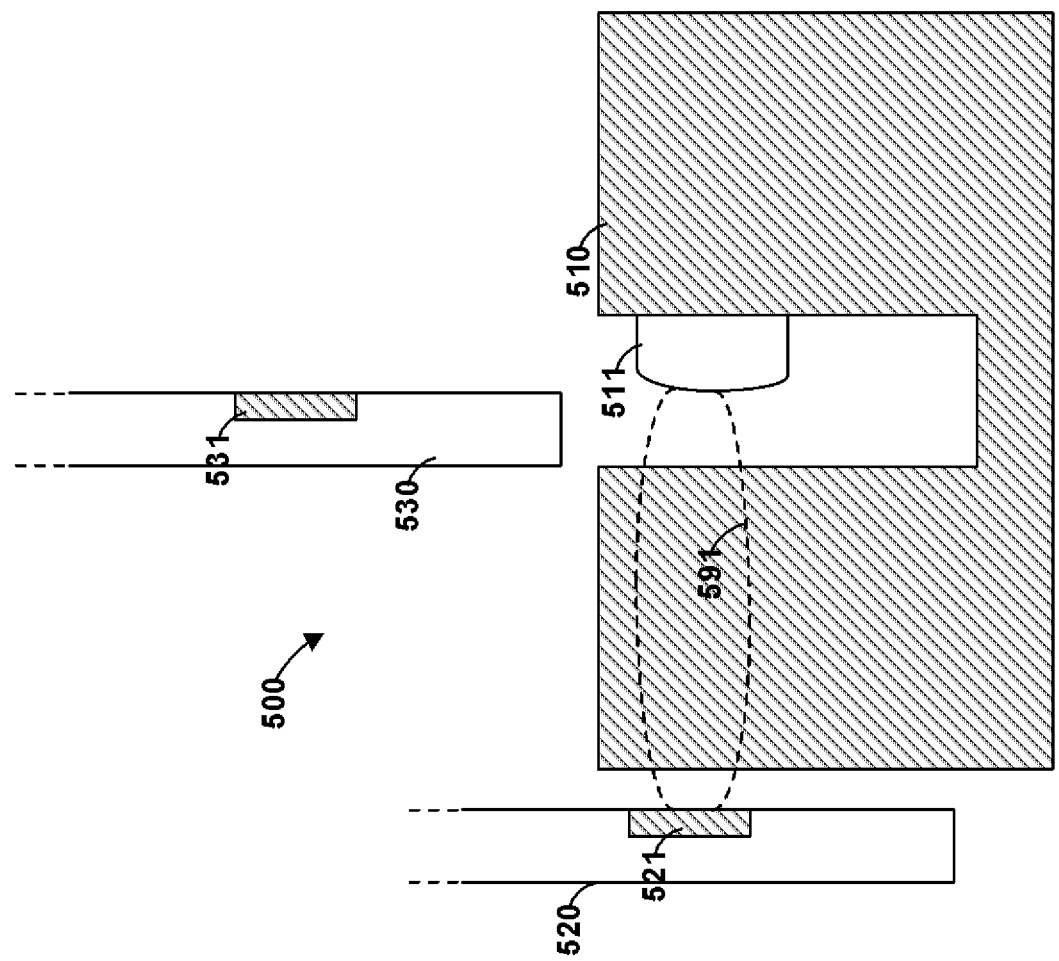
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contactless transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card using, for example, a hot and/or cold lamination. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Persons skilled in the art will appreciate that the direction of current through magnetic circuit 650 may be changed and controlled in a pattern that is representative of magnetic stripe data. Particularly, a processor may, for example, transmit information through a coil by changing the direction of the electromagnetic field generated from emulator circuit at particular times. A change in the frequency of field reversals may be representative of, for example, a particular bit of information (e.g., "1" or "0").

Figure 6:
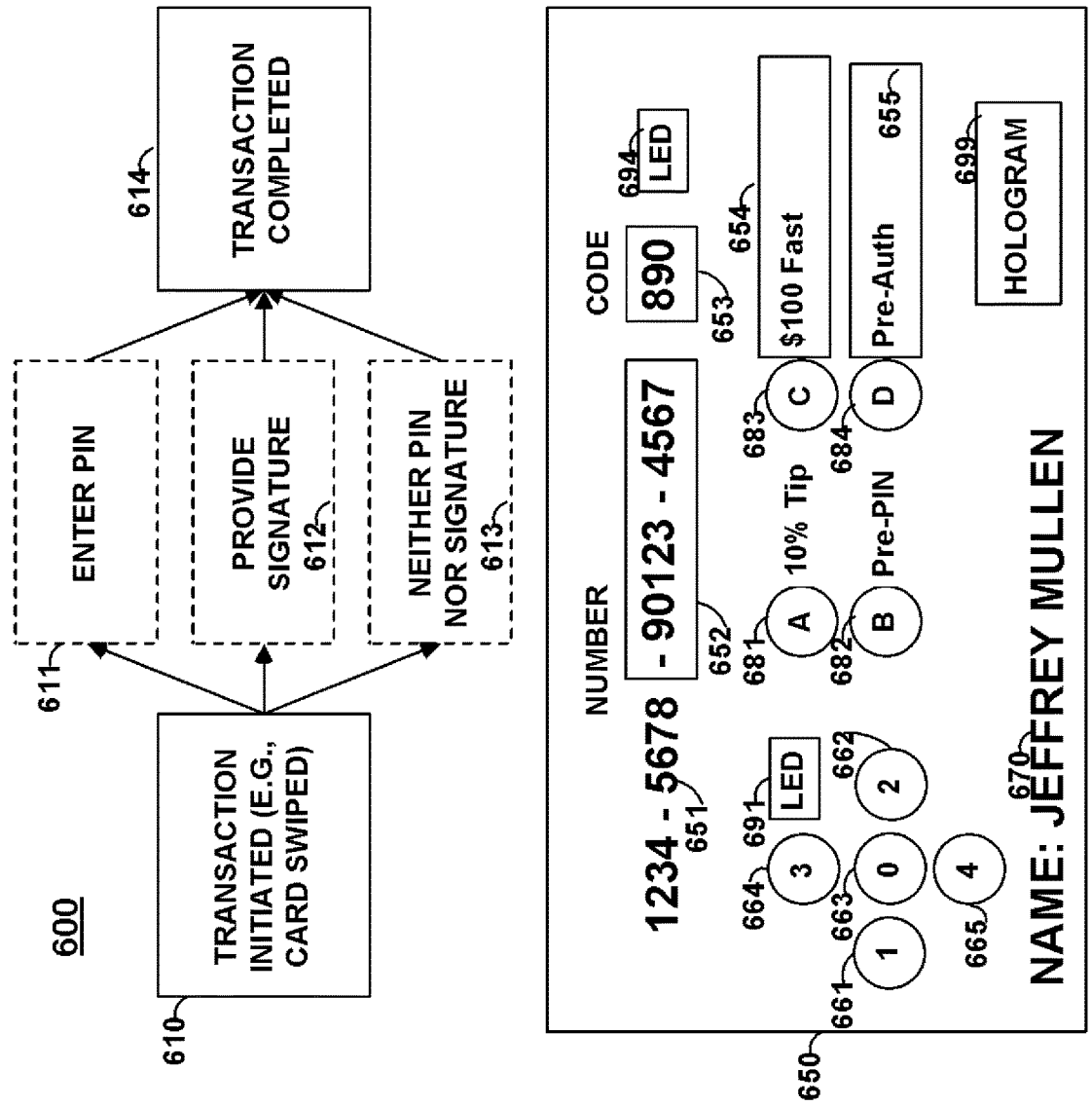
FIG. 6 is an illustration of a card and a payment process constructed in accordance with the principles of the present invention.

FIG. 6 shows card 650 that includes buttons 661-664, light sources 691-694, displays 852-853, permanent information 651 and 670, buttons 681-684, and hologram 699. A user may be provided with a payment number. Such a payment number may be comprised of permanent data, dynamic data, or a combination of permanent and dynamic data. Dynamic data may be provided, for example, on display 652. Display 653 may be utilized to provide a code, which may be dynamic. Such a code may be utilized in authorize a transaction. Persons skilled in the art will appreciate that displays may display a code, payment number, or any type of data that changes based on time or based on use (e.g., utilizes one-time use data). Similarly, data may be static and may not change. Accordingly, for example, a display may be utilized to display the same data when desired such that the data may be hidden when the data is not desired to be displayed. Buttons 651-664, 681-682, and/or 683-684 may be utilized to signal a processor to display information on display 652, display 643, or display 652 and display 653.

A Personal Identification Code (PAC) may be entered to utilize to display data, as well as instruct a processor to provide particular data. For example, a particular PAC may provide one payment number (e.g., a credit card number) while a different PAC may provide a different payment number (e.g., a debit card number). A PAC may include a sequence of button presses (e.g., 5 particular button presses). Furthermore, a PAC may be utilized to unlock a card so that the card may be utilized. For example, buttons 681, 682, 683, and 684 may not be utilized by a user until an appropriate PAC has been entered via buttons 651-665. A number may be changed based on time (e.g., via display 652, display 653, or display 652 and display 653). Accordingly, a PAC may be entered such that the particular number associated with a particular button (e.g., a number associated with button 651) for a particular time period (e.g., a particular day) may be displayed. One PAC may activate display 652 while another PAC may activate display 653.

Light source 691 may be an LED or other source of light. Light source 691 may display light each time a button associated to light source 691 is pressed (e.g., buttons 661-662). Similarly, light source 692 may display light each time a button associated with light source 692 is pressed (e.g., button 681 or 682). Light source 693 may display light each time a button associated with light source 693 is pressed (e.g., light source 683 or 684). Light source 694 may be associated to a component and may display light each time that component is activated (e.g., display 653 or 652 is activated). Light sources may emit light having different colors. For example, a processor may determine that a PAC provided to the processor via buttons 661-665 matches a valid PAC for performing an operation. Each button press may cause light source 691 to emit light of a first color (e.g., YELLOW). The last button press to complete the PAC, however, may cause light source 691 to emit a different color if the PAC is VALID (e.g., emit GREEN) yet emit another color if the PAC is INVALID (e.g., emit RED). Particular areas of a laminated card may be transparent such that light from a light-source illuminates the transparent area.

Persons skilled in the art will appreciate that other default data may be provided to other components of a card upon entry of a PAC. For example, particular default data (e.g., payment card number and discretionary data) may be communicated to a magnetic emulator (or magnetic encoder) such that the information may be communicated to a magnetic stripe read-head. Similarly, default data (e.g., payment card number and discretionary data) may be communicated to an RFID antenna, an IC chip, or an RFID antenna and an IC chip. Such default data may be different for each component (e.g., magnetic encoder/emulator, RFID antenna, IC Chip) and may be in different formats (e.g., one track of payment data for one magnetic emulator and another track of payment data for another magnetic emulator). A code (e.g., the code associated with display 653) may be communicated via a magnetic emulator (or RFID antenna or IC chip). Alternatively, for example, an additional code, which may be dynamic or permanent, may be communicated via a magnetic emulator (or RFID antenna or IC chip). This additional code may be associated with the code associated with display 653 (e.g., associated mathematically). Button 681 may be included on card 650.

Button 681 may cause, for example, display 652, display 653, or display 652 and 653 to display data associated to button 681. Similarly, data associated to button 681 may be communicated through components of card 650 (e.g., a magnetic emulator, magnetic encoder, RFID antenna, and IC chip).

Button 681 may, for example, be associated with a particular amount of a tip (e.g., a 10% tip). Accordingly, for example, a user may interact with button 681 to denote that the user desires to add a tip to a purchase. For example, a user in a restaurant may hand his/her payment card to a waitress and activate button 681 (e.g., after entering in an appropriate PIC into card 650 utilizing buttons 661-665). Accordingly, the waitress may swipe card 650 through a magnetic stripe swipe reader. A read-head detection circuit on card 650 may recognize that card 650 is being swiped. Accordingly, for example, card 650 may communicate information through a magnetic emulator. This information may include payment information (e.g., a payment card number and associated discretionary data). Included in the communicated data may be, for example, data representative of the desired tip amount. Such data may, for example, be a flag (e.g., a particular character in a particular location of communicated data). A system, such as a cash register or remote server, may recognize the flag and may authorize a payment transaction associated with the total amount of a purchase (e.g., the amount after the desired tip has been added).

Button 682 may be associated to, for example, a pre-ATM activity. Such a pre-ATM activity may be, for example, a pre-PIN activity. For example, a user may activate button 682 and utilize buttons 661-665 to enter in the user's PIN. The user may then, for example, place card 650 in the proximity of a card reader such that payment information and a user's PIN may be communicated through a magnetic emulator (or communicated through an RFID antenna and/or IC chip). Accordingly, a user may enter in his/her PIN into a payment card such that a user does not have to enter his/her PIN into an ATM. In doing so, for example, a user may more securely enter in his/her PIN (e.g., by hiding a card) as well as accelerate an ATM activity (e.g., by entering a PIN while waiting in line for an ATM). A user may enter his/her PIN into card 650 utilizing buttons 661-665 and then, for example, press button 682 to cause a processor to place the entered PIN information into data communicated from card 650. Accordingly, for example, the sequence of buttons 661-665 that are pressed may be stored in a memory of card 650 and utilized by a processor of card 650.

Button 683 may be associated to display 654. Alternatively, for example, button 683 may be associated with written and/or embossed information (not shown). For example, button 683 may be associated to display 654. Display 654 may display data associated with a particular card function. For example, display 654 may display a fast-cash function (e.g., $100 fast cash). A user may utilize interfaces on card 650 (e.g., buttons 651-662) to set or change the information displayed on display 683. A user may enter in a card configuration on a computer and receive information into the card from the computer, in a variety of ways, in order to configure the card (e.g., to display a particular function on display 654). For example, a user may swipe card 650 and receive information through a coil from a magnetic encoding head that generates an electromagnetic field. Alternatively, for example, a processor may receive configuration information via an RFID antenna and/or an IC chip.

Button 683 may be associated with a fast-cash function. A user may interact with button 683 to provide an instruction to a processor that a fast-cash functionality is desired. A user may, for example, enter his/her PIN into a card. After the user's PIN is verified by a processor on card 650, a user may, for example, press button 683 such that a flag is communicated through transmitted payment information representative of a fast-cash function. Accordingly, for example, an ATM (or other device) may receive payment information that may include a fast-cash flag. The machine may also receive PIN information from a card. The machine may utilize a payment card number in the payment information with the PIN number to verify the identity of the user. The machine may recognize the received flag and utilize the flag as control data to dispense cash to the user. Accordingly, for example, a user may perform ATM activities on a card while waiting in line for an ATM in order to minimize the amount of time a user is required to interact with that ATM.

Button 684 may be associated with display 684 and a pre-authorization functionality. For example, a pre-authorization functionality may be utilized to pre-authorize a particular amount or to complete a signature-based transaction without a signature. For example, a tip amount may be added to a total amount and may be pre-authorized. Accordingly, a user may receive a receipt that requires his/her signature with the pre-authorized total amount (that includes the tip). Additionally, for example, a PIN may be entered utilizing buttons 661-665 and button 684 may be utilized to communicate the PIN as a pre-authorization. Accordingly, a remote server may receive payment information that may include at least a PIN, a payment number, discretionary data, and a flag associated that the PIN is desired to be utilized in lieu of a signature as a form of authorization for the transaction.

Flow chart 600 may be utilized in conjunction with a payment card, such as payment card 650. Step 610 may be included in flow chart 600. Particularly, for example, step 610 may be initiated when information is communicated from a payment card, through a payment card reader, through a payment card routing server, to a payment card authorization server. Step 611 may be included, in which a PIN is requested to be entered at a reader. Step 612 may be included, in which a signature is requested to be entered in a reader. Step 613 may be included, in which a PIN, for example, is communicated to a remote server via a card, thus not requiring either a PIN or a signature to be entered on a payment card reader. A payment transaction may be completed in step 614

Persons skilled in the art will appreciate that a pre-authorization activity may include the pressing of a single button after an appropriate PIN has been entered into a card. Accordingly, the card may authorize a user and may communicate an appropriate flag when payment data is communicated from a card. Accordingly, a remote server may receive a flag. The remote server may authorize a payment transaction based on the received data that includes the flag, indicative of an appropriate PIN entered into a card and the activation of a button associated with a pre-authorization activity.

Figure 7:
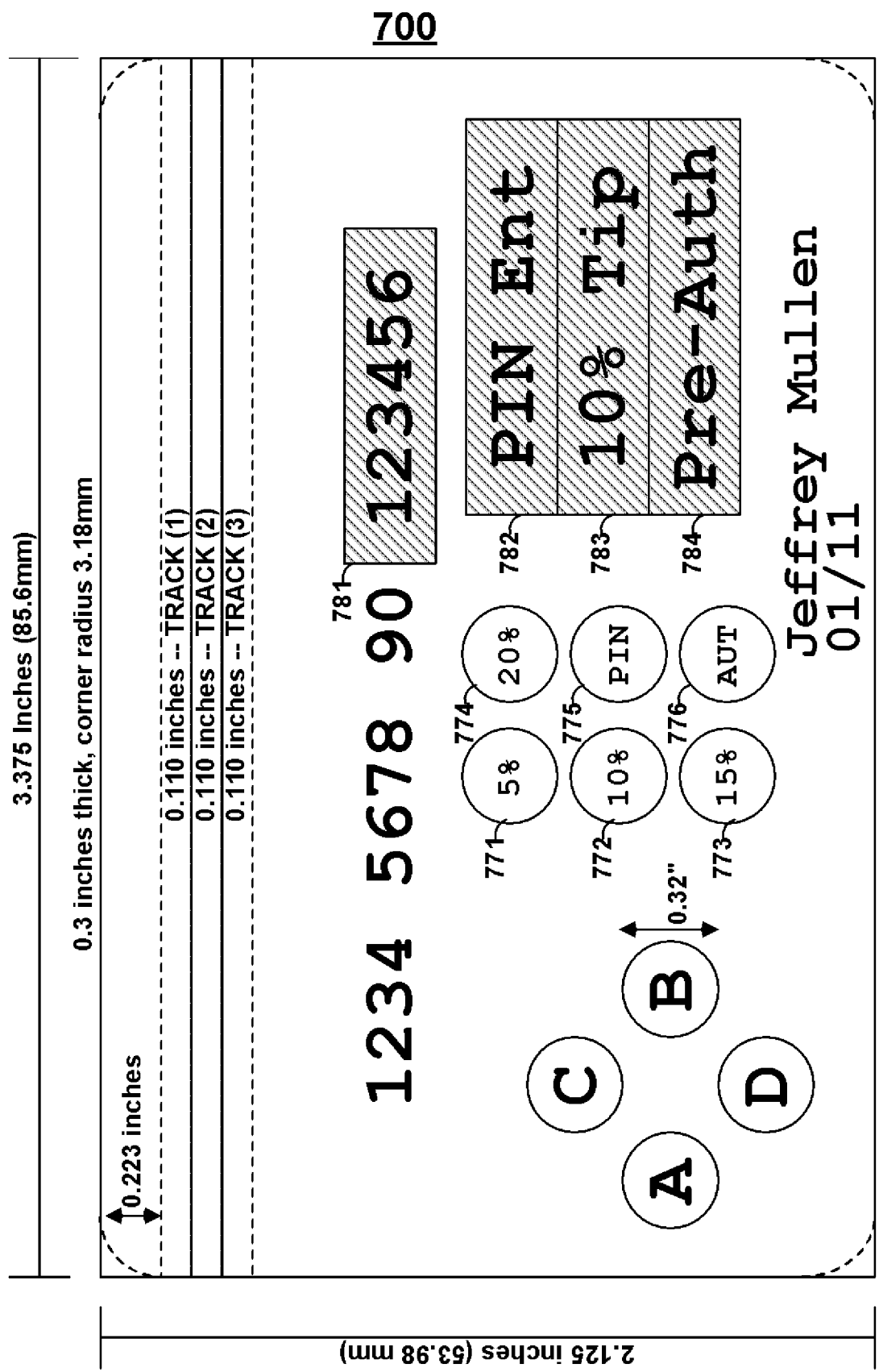
FIG. 7 is an illustration of a payment card constructed in accordance with the principles of the present invention.

FIG. 7 shows card 700. User interface 771 may be included on card 700 and may be associated to a particular tip percentage (e.g., 5%). User interface 772 may be included on card 700 and may be associated to a different tip percentage (e.g., 10%). User interface 773 may be included on card 700 and may be associated to another tip percentage (e.g., 15%). User interface 774 may be included on card 700 and may be associated to yet another tip percentage (e.g., 20%). User interface 775 may be included on card 700 and may be associated to the desire to enter a PIN into card 700. User interface 776 may be included on cad 700 and may be associated to an authorization activity. Displays 781-784 may be utilized to display information. For example, display 781 may display payment card information (e.g., after an appropriate PIN is entered into card 700). Display 782-784 may be utilized to display selected combinations of activities. For example, if a user is in a restaurant, a user may enter a PIN, enter that the PIN should be utilized for payment authorization, and that a 10% tip is authorized. Persons skilled in the art will appreciate that a user may utilize buttons to enter in a PIN at any time (e.g., without pressing a button indicating a PIN is about to be entered) and a correct entry of a PIN may result in a display (e.g., display 782) displaying indicia associated with the correct entry of a PIN.

Figure 8:
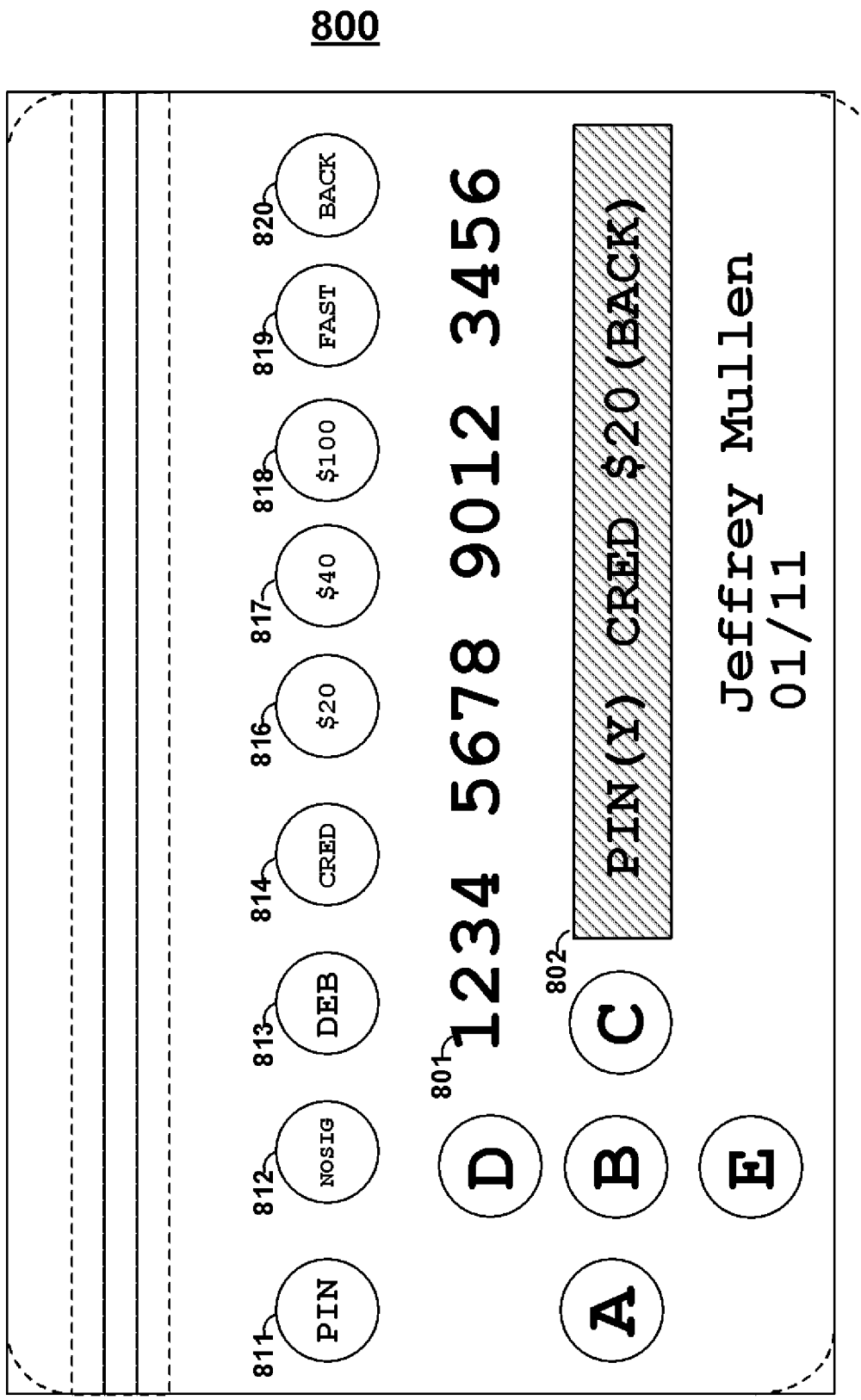
FIG. 8 is an illustration of a payment card with multiple user interfaces constructed in accordance with the principles of the present invention.

FIG. 8 shows card 800 that may include, for example, user interfaces 811-820. User interfaces 811-820 may be a button such as a mechanical button or a capacitive button.

User interface 811 may be pressed by a user to instruct a processor on card 800 that a user desires to enter a PIN into card 800 utilizing user interfaces located on card 800. Accordingly, a user may interface with user interface 811. The user may then enter his/her PIN into user interfaces of card 800. The entered PIN may then be, for example, stored and verified by a processor of card 800. Persons skilled in the art will appreciate, however, that a PIN entered by a user does not need to be verified by card 800. An entered PIN may, for example, be stored and the entered PIN may be communicated to a remote device by card 800. Accordingly, a PIN may be verified by remote devices A PIN may be verified by card 800 in addition to being forwarded to a remote device for verification.

Card 800 may include user interface 812. A user may interface with user interface 812 (e.g., press a mechanical button) and cause a processor of card 800 to implement a functionality associated with user interface 812. Such a functionality may include, for example, instructions to communicate information associated with the desired functionality when card 800 communicates information to external devices (e.g., a payment card magnetic stripe reader, IC chip reader, or RFID reader). User interface 812 may, for example, cause information to be sent indicative of a user's desire to complete a signature-based transaction without a signature. Accordingly, for example, card 800 may communicate information that includes a payment card number, the PIN entered into card 800 by a user, and a data indicative of the user's desire to utilize the entered PIN to complete a transaction instead of utilizing a signature.

User interface 813 may be associated to a particular type of card. For example, user interface 813 may be associated to a particular type of a payment card (e.g., credit payment, debit payment, gift payment). Accordingly, for example, a user may interact with user interface 813 to instruct a processor that the user desires to utilize a particular type of payment for a purchase. Multiple interfaces may be included on card 800 and each interface may be associated to a different type of payment. For example, user interface 814 may be included on card 800 and may be associated with a credit payment. A processor may receive a control signal from user interface 813. The processor may then retrieve payment information associated with stored payment information for user interface 813. Accordingly, for example, the processor may retrieve debit card information (e.g., a debit card account number and associated discretionary data). The processor may then communicate this retrieved information from card 800. Persons skilled in the art will appreciate that the card may communicate payment information in different forms depending on the type of reader the card interfaces with. For example, card 800 may detect that card 800 is placed in a magnetic stripe swipe reader and may communicate the payment information desired by the user in the form of track 1 and track 2 magnetic stripe data. Card 800 may alternatively, for example, detect that card 800 is placed in an electromagnetic field and may communicate the appropriate payment information as an RFID signal from an RFID antenna located on card 800.

User interfaces 816-818 may be associated to particular dollar amounts. User interfaces 819 and 820 may be associated to functions that are based on particular dollar amounts. Accordingly, for example, a user may select a user interface 816-818 as well as user interface 819 or 820 in order to provide a combinational instruction to a processor. For example, a user may utilize user interface 819 and 818 to instruct a processor that a fast-cash functionality is desired in the amount of $100. As per another example, a user may utilize user interface 820 and 818 to instruct a processor that a cash-back functionality is desired in the amount of $100. Accordingly, a user may utilize user interfaces to provide combinational logic in order to, for example, reduce the number of user interfaces on a card. In reducing the number of user interfaces on a card, for example, the cost of a card may be decreased. Persons skilled in the art will appreciate that a cash-back and a fast-cash functionality may be provided with a single button. A single flag may be placed in data outputted in a card indicative of the desire to utilize a fast-cash and cash-back functionality. A remote device, such as a cash register), may recognize the flag and may perform the desired operation if, for example, the machine is only capable of providing one of the two options (e.g., fast-cash or cash-back). A button may be pressed multiple times to toggle between different options. For example, a button may be pressed once to toggle to a fast-cash functionality while the same button may be pressed again to toggle to a cash-back functionality.

The results of user selections may be displayed, for example, on display 802. Accordingly, for example, a user may visually verify that card 800 has correctly received the user's desired selections. Permanent information 801 may be provided. Permanent information 801 may include, for example, a payment card number, a user's name, a verification code, an expiration date, instructions for destroying a card, and instructions for using a card. Person skilled in the art will appreciate that permanent information 801 may include a default payment card number (e.g., a first credit card number). The use of user interface 814 may, for example, cause a secondary credit card number to be displayed on display 802. A card that is used with a reader without receiving any information from a user via user interfaces may, for example, communicate default information (e.g., default payment information or information indicative that a user has not entered any information into a card utilizing user interfaces located on the card).

Figure 9:
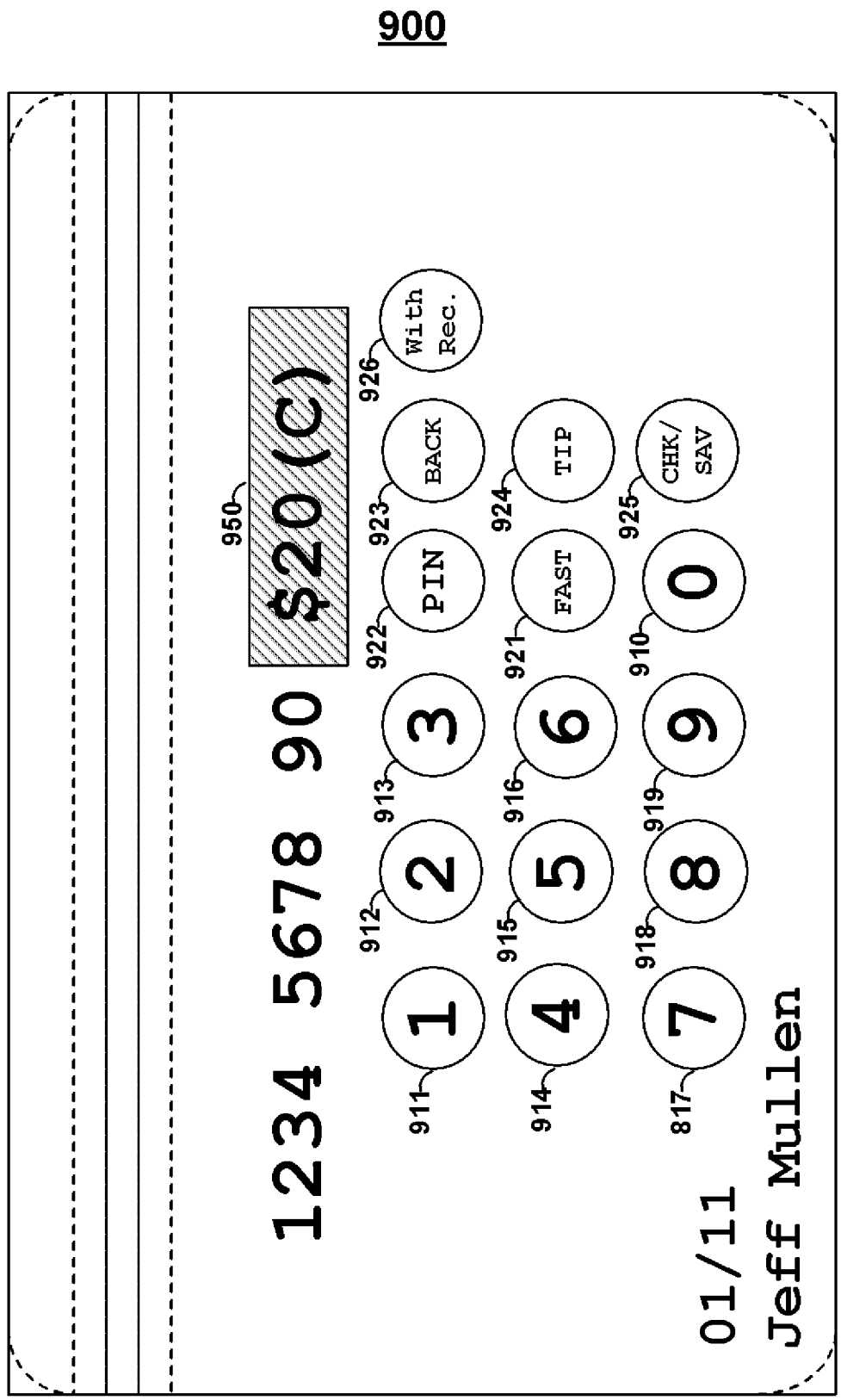
FIG. 9 is an illustration of a payment card constructed in accordance with the principles of the present invention.

FIG. 9 shows card 900. Card 900 may include, for example, user interfaces 911-910 and 922-925. Card 900 may also include, for example, display 650. User interfaces 910 to 919 may each be associated to, for example, a digit. Accordingly, for example, user interfaces 910-919 may form a ten digit numeric keypad. This keypad may be utilized by a user to communicate numerical information to a processor. Multiple functions may, for example, utilize numerical information. For example, user interface 922 may be associated with a PIN-entry function. Accordingly, a user may use interface 922 and then the user may enter a PIN into card 900 by utilizing interfaces 911-919. User interface 921 may be associated with a fast-cash functionality. Accordingly, a user may select fast-cash by utilizing interface 921 and then may enter in the desired amount of cash the user desires to withdrawal utilizing interfaces 910-919. A confirmation step may be utilized. For example, a user may interface with button 921 before and after selecting a withdrawal amount. Display 650 may, for example, display an updated selection status after, for example, a function button is pressed a second time (e.g., after numerical information is entered). Alternatively, for example, a user selection may be presented via display 650 after the numerical information was entered by a user such that a user can press a function button a second time, after viewing the displayed selection, to confirm the selection. A user may reset the selection by, for example, entering a different numerical amount utilizing user interfaces 910-919. In doing so, for example, a user may easily correct a situation where the user entered the wrong numerical information into card 900.

User interface 923 may be associated with, for example, a cash-back functionality. Accordingly, a user waiting in line to purchase an item may select cash-back utilizing interface 923 and may enter in an amount of desired cash-back. This request may be communicated from the card to a cash register such that the cashier is notified to provide the desired amount of cash-back to the user. Accordingly, a transaction may be authorized for the amount of the purchase as well as the amount of the cash withdrawal. User interface 924 may be associated to a tip and user interfaces 911-919 may be utilized to enter in the desired tip. Persons skilled in the art will appreciate that a card, or a remote device, may utilize numerical information as a percentage (e.g., 10%) or as a number (e.g., $10). A user interface may be provided for a decimal place such that cents information may be entered into a card by a user. User interface 925 may be utilized by a user to toggle between a checking account and a saving account. User interface 926 may be utilized to notify the card that a user desires a receipt. Accordingly, information may be communicated by the card to a point-of-sale device to indicate that the user desires a receipt. In doing so, for example, the amount of user-to-cashier verbal interaction may be minimized. A user may utilize user interface 926 to toggle between a state of desiring a receipt to a state of not desiring a receipt. Information indicative of a user's selection may be displayed, for example, on display 950. For example, "$20(C)" may denote that a user selected to withdrawal $20 from his/her checking account.

Figure 10:
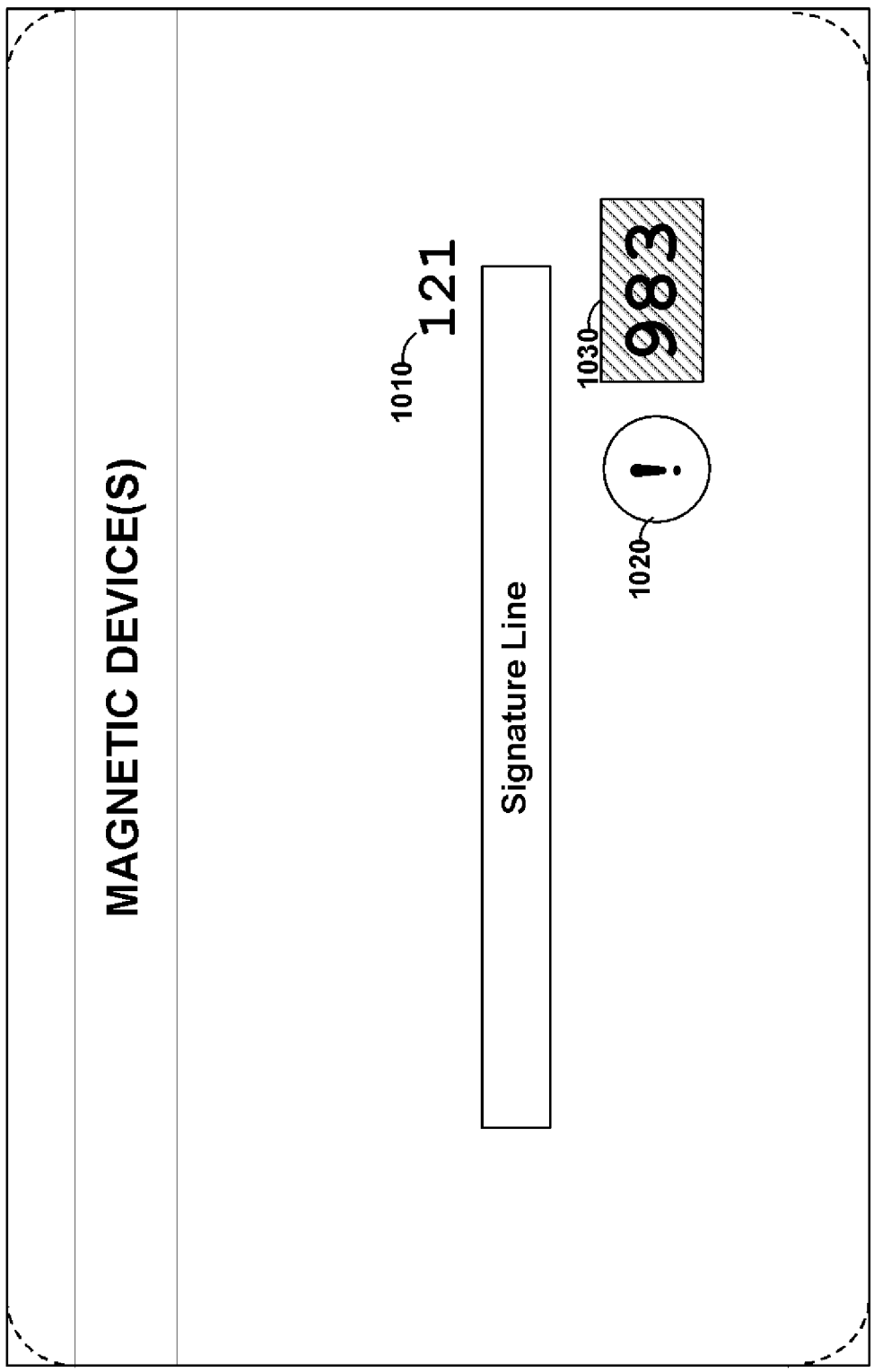
FIG. 10 is an illustration of a card and a portion operable to receive a written signature constructed in accordance with the principles of the present invention.

FIG. 10 shows card 1000. Card 1000 may include, for example, an reverse side that includes a material operable to receive a user's signature (e.g., a pen-based signature). The reverse side may also include code 1010. Code 1010 may be displayed on a display located on a reverse and/or obverse side. Code 1010 may be electronically communicated by a card (e.g., via an IC chip, a magnetic emulator/encoder, and/or an RFID antenna). Persons skilled in the art will appreciate that any interface, display, or other component of a card may be located on the reverse or obverse side of the card. Display 1030 may include a code that is displayed upon interaction with interface 1020. Display 1030 may not, for example, display information until, for example, a correct PIN has been entered into interfaces located on the obverse side of the card and interface 1020 has been utilized by a user. The code displayed on display 1030 may be communicated through a magnetic emulator/encoder in one or more tracks of magnetic stripe data.

Figure 11:
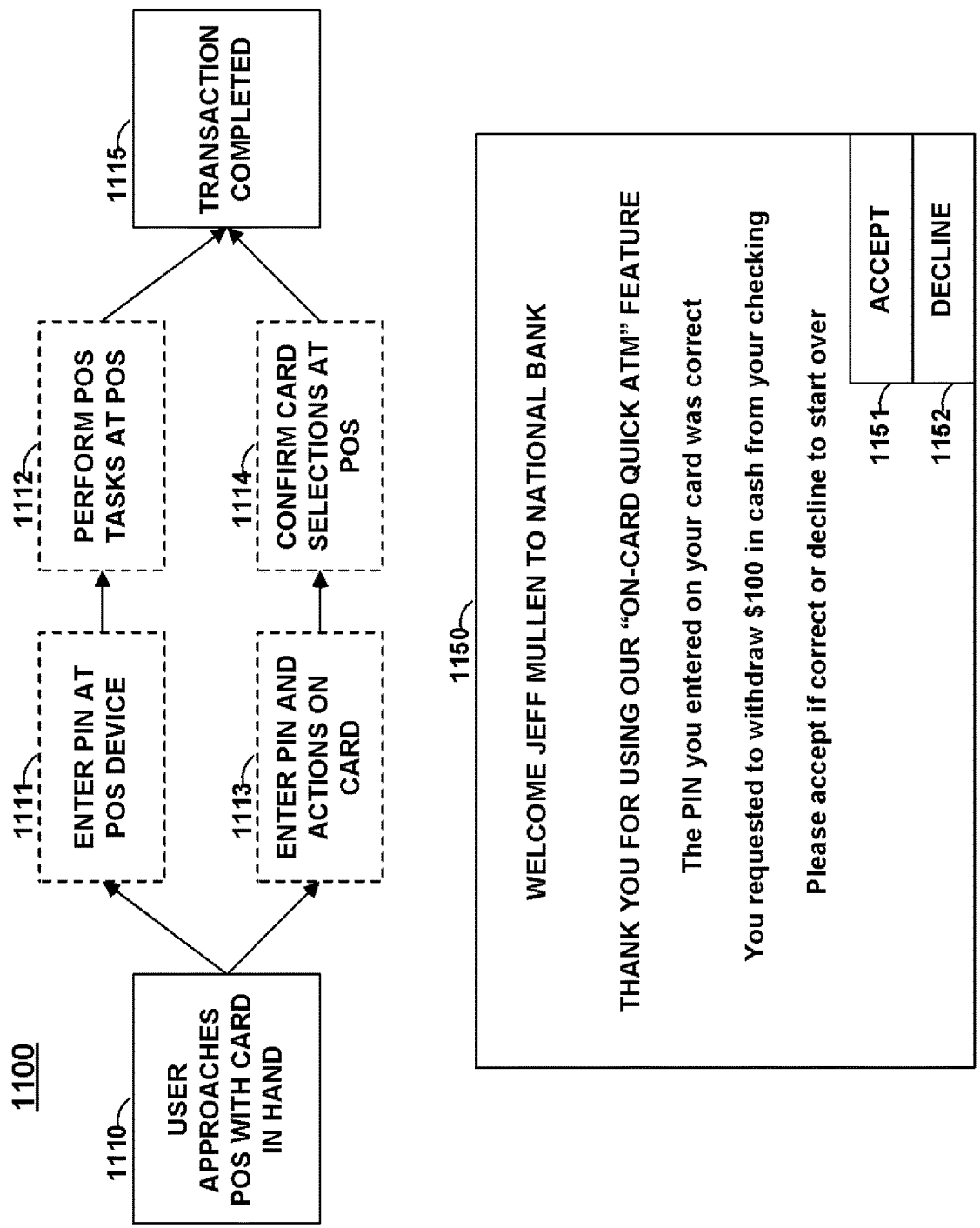
FIG. 11 is an illustration of a payment process and a graphical user interface constructed with the principles of the present invention.

FIG. 11 shows flow chart 1100 and graphical user interface 1150. Flow chart 1100 may include, for example, step 1110, in which a user approaches a point-of-sale device with a payment card. Step 1111 may be provided that includes a user entering his/her PIN on the point-of-sale device. Accordingly, a user may perform associated tasks at the point-of-sale device in step 1112. The transaction may be completed at step 1115. Alternatively, for example, the user may enter his/her PIN and/or other point-of-sale decisions on his/her card in step 1113. A user may confirm the selections the user entered into his/her card at the point-of-sale in step 1114 after the card communicates the user's decisions to the point-of-sale device. The transaction may be completed in step 1115.

Graphical user interface 1150 may be provided on a display of a point-of-sale device. A point-of-sale device may include, for example, a cash-register, a payment card reader, and an ATM. Graphical user interface may include interfaces 1151 and 1152 for receiving manual input. Buttons may be provided on a point-of-sale device to receive user input. A card may display a graphical user interface and may include, for example, a capacitive touch screen such that a user may interact with interface areas of the touch screen in order to enter manual input into the touch screen. An ATM may include a graphical user interface to, for example, display a user's decisions that were entered into a card and communicated to the ATM via an output communications component (e.g., a magnetic emulator, RFID antenna, or IC chip).

Figure 12:
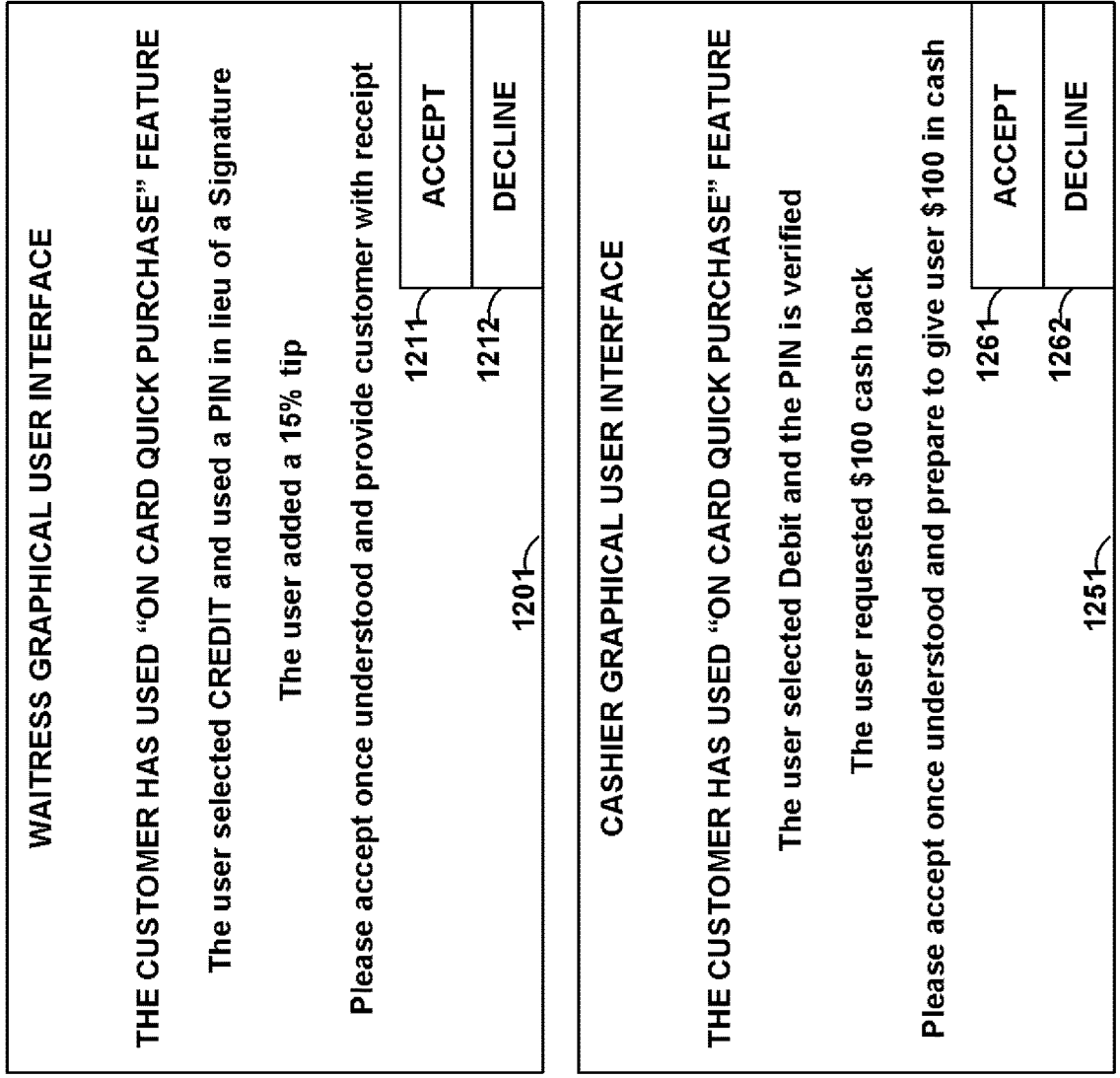
FIG. 12 is an illustration of graphical user interfaces constructed in accordance with the principles of the present invention.

FIG. 12 shows graphical user interface 1201 that may include manual input interface 1211 and 1212 and graphical user interface 1251 that may include manual input interface 1261 and 1262. Graphical user interface 1201 may be provided on a display of a point-of-sale devices such that an operator of the point-of-sale device may be provided with the decisions of a the user of a card. The operator may acknowledge that the operator understands the user's selection by utilizing manual input interfaces 1211 and 1212. A point-of-sale device, such as a cash-register may perform a number of functions after an operator acknowledges understanding of a user's decisions. For example, a cash-register may cause a cash drawer to open such that an operator may remove cash from the drawer and hand the cash to a user (e.g., to complete a cash-back transaction).

Figure 13:
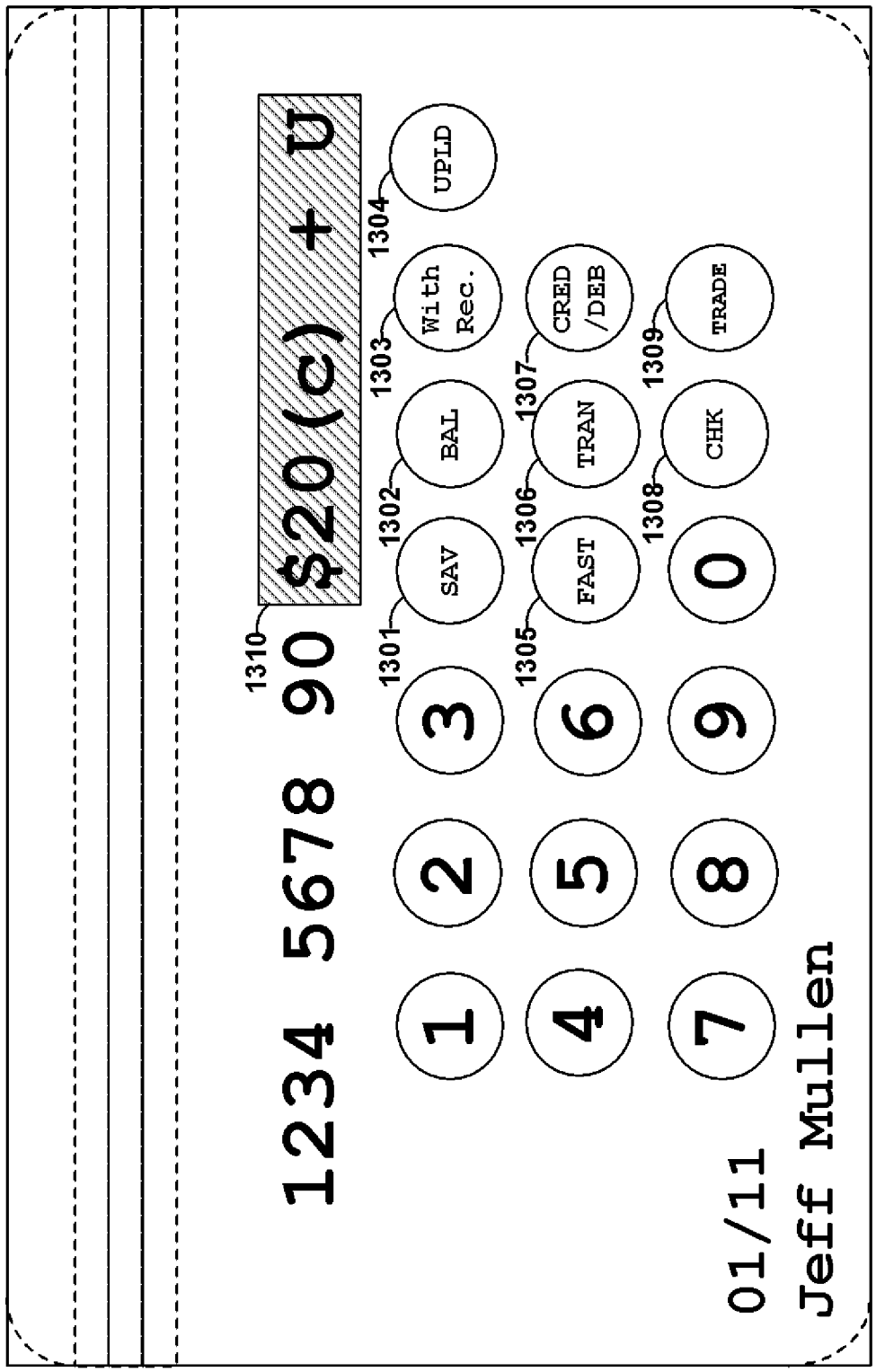
FIG. 13 is an illustration of a payment card constructed in accordance with the principles of the present invention.

FIG. 13 shows card 1300 that may include user interfaces 1301-1309 and display 1310. A user may utilize interface 1302 to utilize a savings account. A user may utilize interface 1305 to utilize a fast-cash withdrawal function. A user may utilize interface 1302 to obtain a balance receipt. A user may utilize interface 1306 to conduct a transfer operation. A user may utilize interface 1308 to utilize a checking account. A user may utilize interface 1303 to note that a receipt is desired. A user may utilize interface 1307 to toggle between a credit and debit account. A user may utilize interface 1309 to instruct an ATM, for example, to provide the first graphical user interface as a stock-trading interface. User may utilize interface 1304 to initiate an upload feature. Display 1310 may note a user's selections (e.g., $20 withdrawal from a checking account followed by an upload operation).

A card may receive information in a variety of ways. For example, a card may receive information from an RFID antenna, an IC chip, or a magnetic emulator. For example, a magnetic stripe encoder on a point-of-sale device may communicate information to a coil located on a card. Thus, information may be communicated from a point-of-sale device to a card. A user may utilize interface 1304 to instruct a card to prepare for an upload function (e.g., a card operating a contact or coil in a receive mode instead of a transmit mode). Balance information, latest transaction information, or any other type of information may be communicated to a card and displayed on display 1310. Information may be uploaded to a card via audio signals received by an on-card microphone or light signals received by an on-card light sensor. A user may utilize a combination of buttons to provide a combinational decision. For example, a user may utilize interface 1301, then interface 1306, then numerical interfaces to enter in the number "100," then interface 1308 to instruct the card that the user desires an ATM machine to transfer $100 from the user's savings account to the user's checking account.

Figure 14:
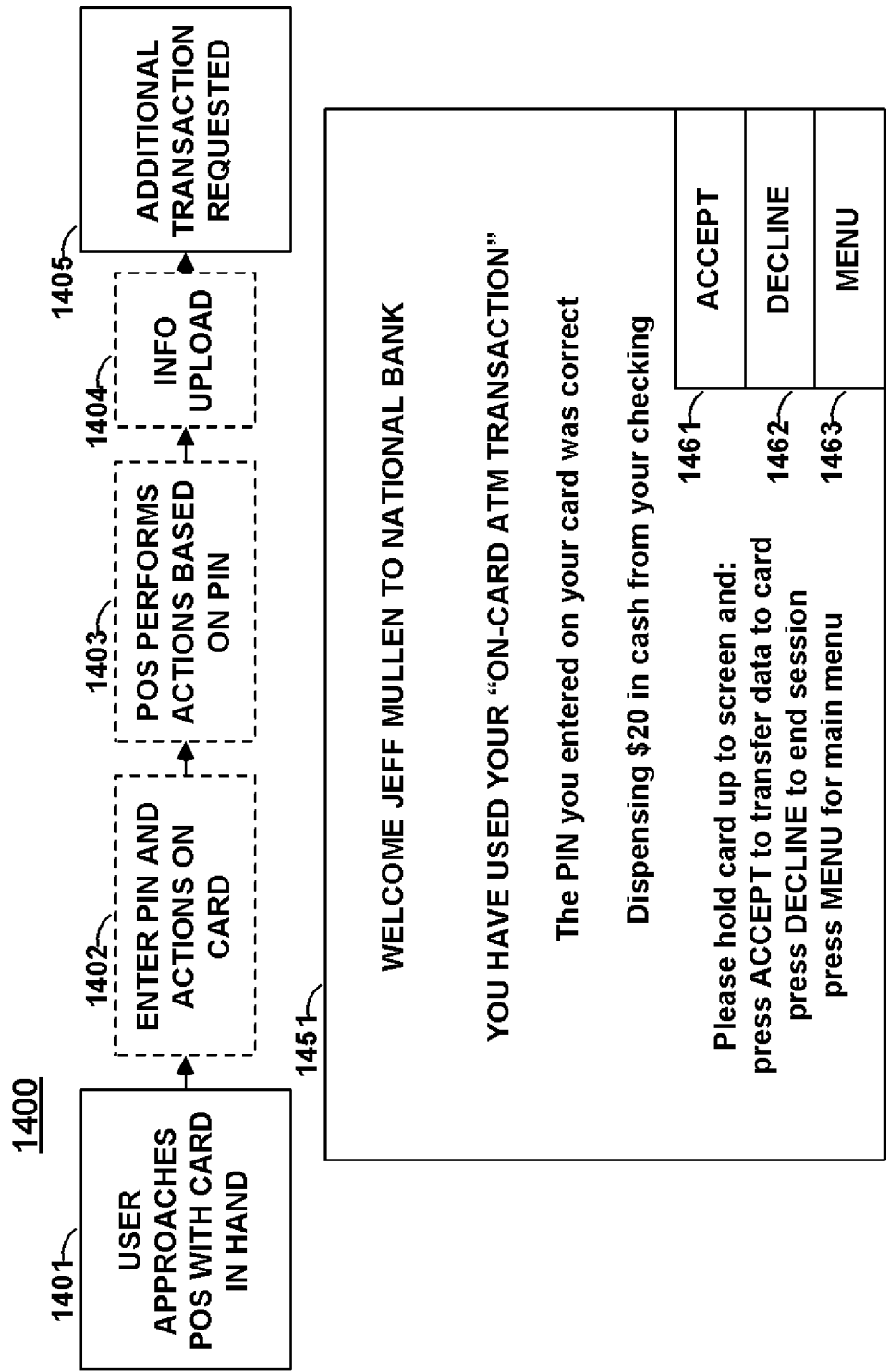
FIG. 14 is an illustration of a flow chart of a payment process and a graphical user interface associated with the principles of the present invention.

FIG. 14 shows flow chart 1400 and graphical user interface 1451. Flow chart 1400 may include step 1401, in which a user approaches a point-of-sale with a card. The user enters his/her decisions into a card in step 1402. Step 1403 occurs, in which the point-of-sale performs actions based on the actions and PIN received from the user's card. Step 1404 may then occur, in which information is uploaded from the point-of-sale to the card. An additional transaction may occur in step 1405. Graphical user interface 1451 may be included with manual input interfaces 1461, 1462, and 1463. Interface 1463 may take a user to an options menu. A display screen may communicate information from a point-of-sale device (e.g., an ATM) to a card.

A light detector may be provided on a card that may receive light pulses indicative of data. Accordingly, for example, a user may hold a card up to a display—such as the screen of a laptop, stationary computer, or mobile phone—and information may be communicated from the display to the card via the light detector. Similarly, a light source may be utilized to communicate information from one device to another. For example, a light source (e.g., LED) may be utilized to communicate information from one card to another. Similarly, a magnetic stripe reader may include a light source. A card may be positioned over the light source such that a light detector of the card is aligned with the light source to receive light. Accordingly, the light of a magnetic stripe reader (or other type of reader) may be utilized to communicate information back to a card. A user may utilize interfaces on the card (e.g., buttons) to initiate a transfer of data from one card to another card or from a device to a card. A variety of types of data may be communicated. For example, money may be communicated from one debit card to another debit card such that payments may occur between the cards. Accordingly, for example, the next time a card is utilized via a reader (e.g., a magnetic stripe reader) information of the transfer may be communicated to a server for processing. Light may be utilized to transfer data from a card to a computer using, for example, a camera (e.g., webcam) on the computer.

Figure 15:
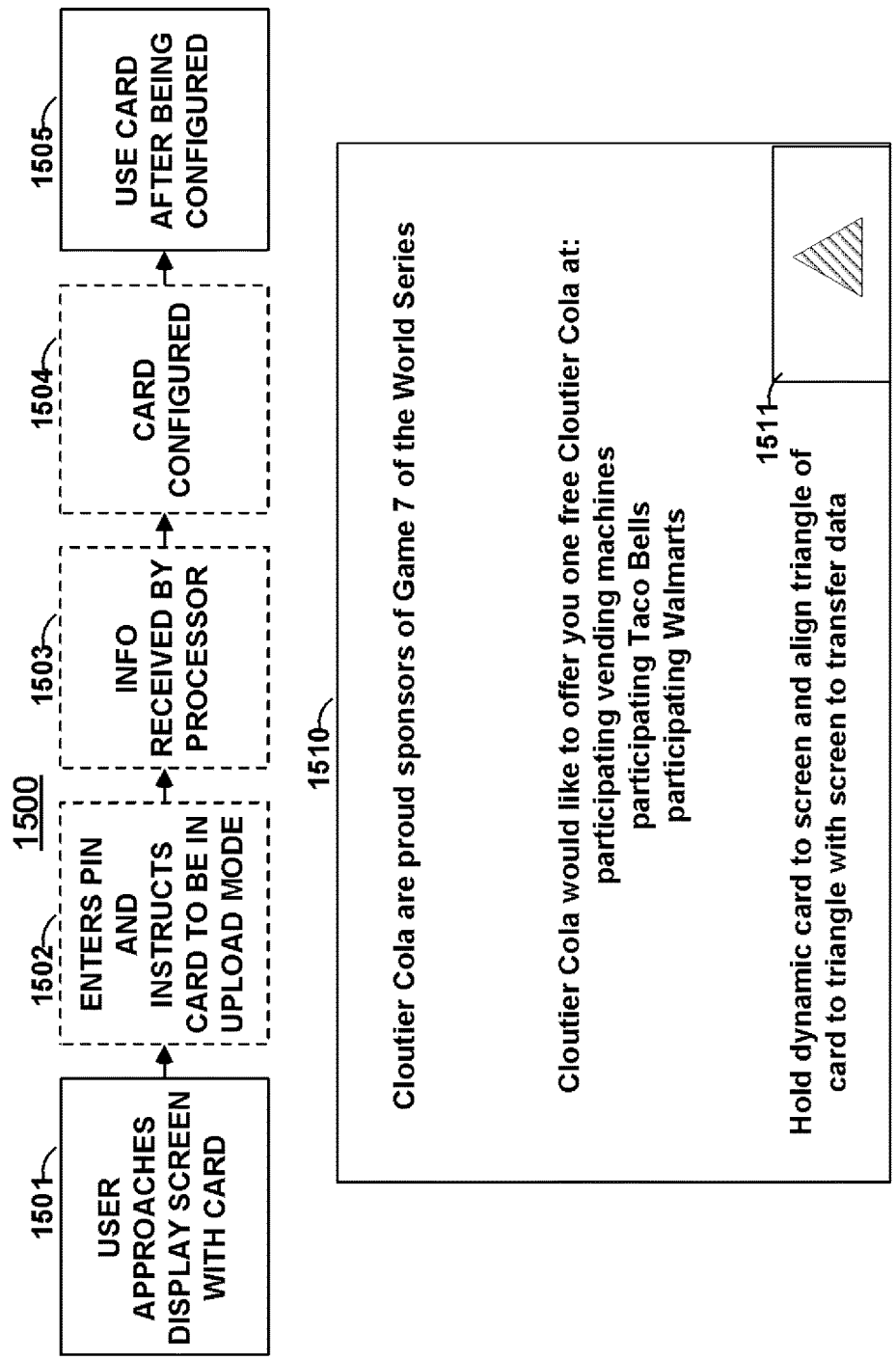
FIG. 15 is an illustration of a flow chart of a payment process and a communications interface constructed in accordance with the principles of the present invention.

FIG. 15 shows flow chart 1500 and graphical user interface 1510. Flow chart 1500 may include step 1501, in which a user approaches a card-reader having a display with a card. The user may enter his/her PIN into the card and provide instructions to the card in step 1502. Particularly, for example, a user can instruct the card to operate in an upload mode. Step 1503 may initiate in which information is received by the processor of a card from a point-of-sale device. The card may configure itself depending on the received information in step 1504. Step 1505 may occur in which the card is used by a user after the card is configured.

Display screen 1510 may be provided. For example, display screen 1510 may be provided to communicate information to a card. For example, area 1511 may communicate information to a light sensor located on a card by providing light pulses that may be understood as information by a processor located on a card. Area 1511 may be provided on any type of display. For example, area 1511 may be provided during a commercial or during a television show. Alternatively, for example, area 1511 may be provided on a webpage. Information that may be communicated through area 1511 may include, for example, coupons that may be utilized at various point-of-sale devices. For example, a cola commercial may communicate a coupon for a free bottle of cola.

Figure 16:
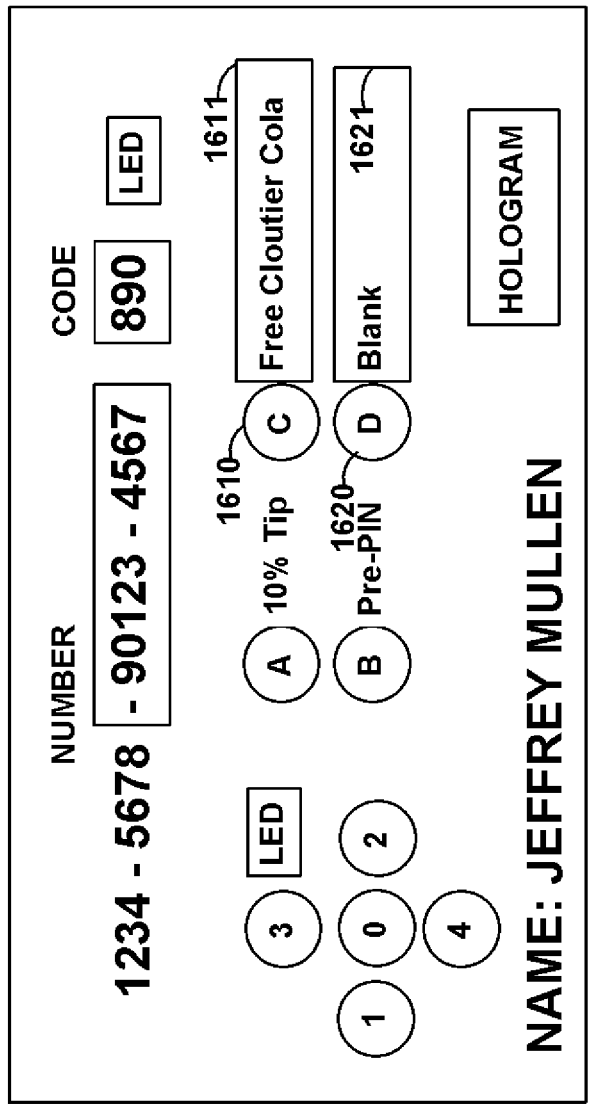
FIG. 16 is an illustration of a card constructed in accordance with the principles of the present invention.

FIG. 16 shows card 1600 that may include, for example, button 1610, display 1611, button 1620, and display 1621. Persons skilled in the art will appreciate that a card may receive coupon information (e.g., from a light-emitting area on a commercial or webpage). The coupon information may include information to display on a display of a card as well as information to communicate to a reader when the coupon is desired to be used (e.g., via activation of button 1610). For example, a coupon code may be communicate via a magnetic emulator. Received coupons may expire after a period of time and may be erased from a card's memory. The time may be set by the coupon issuer and communicated to a card. A card may keep a list of displays that do not have a coupon associated with them and may, for example, display a newly received coupon in the next available display. Displays may be kept OFF until, for example, a user enters a PIN into a card and the card verifies the PIN. Multiple coupons may be associated with a display and a user may toggle through the coupons by pressing a button associated with the display. A user may select a coupon by, for example, holding a button down for a period of time (e.g., more than 2 seconds).

Figure 17:
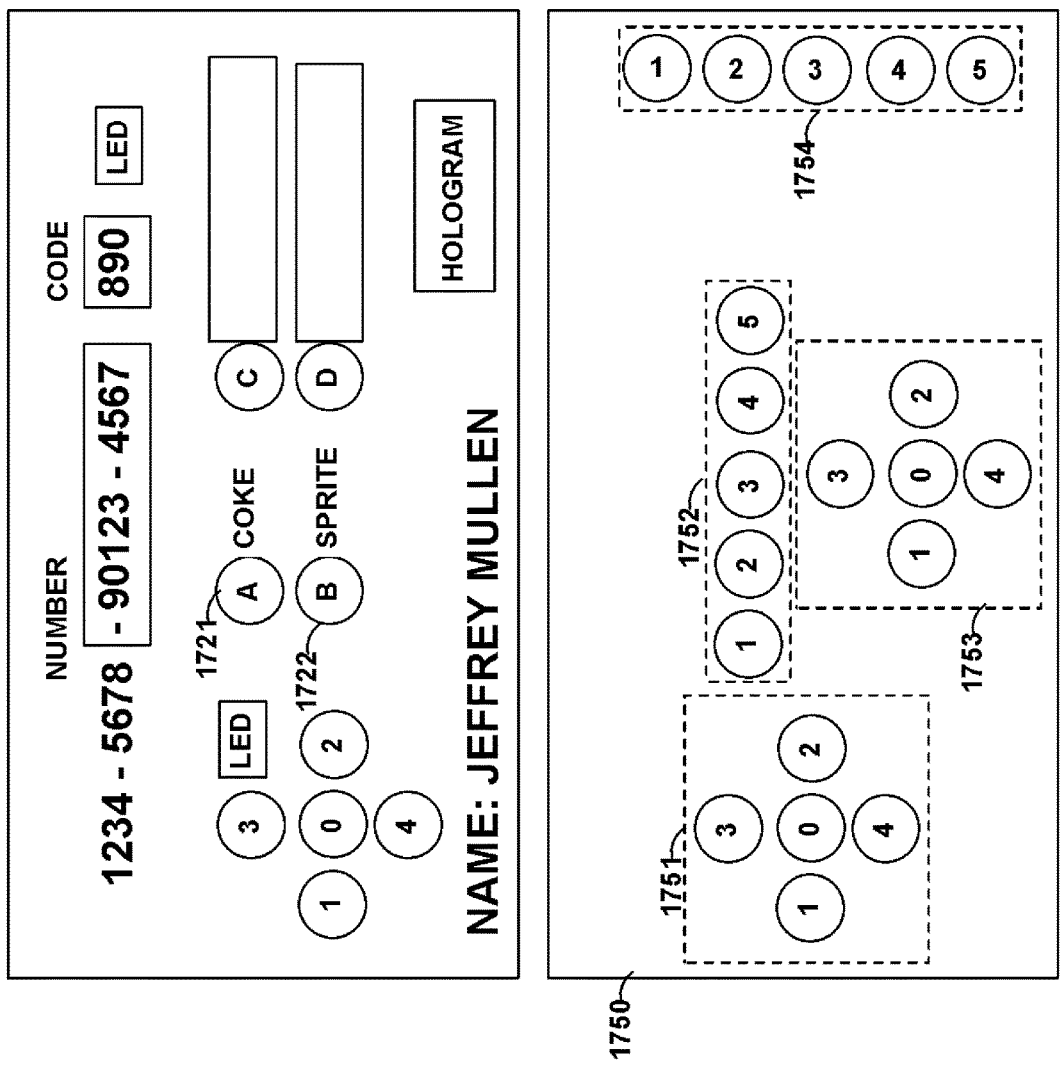
FIG. 17 is an illustration of a card that includes user interfaces for ordering items constructed in accordance with the principles of the present invention.

FIG. 17 shows card 1700 that may include buttons 1721 and 1722. A card may include buttons associated with, for example, particular items. A user may select such items and utilize the card at a vending machine. The vending machine may receive both payment information and ordering information. Accordingly, a user waiting in line to utilize a vending machine may select a button associated with cola and may simply swipe his/her card when the user approaches the vending machine. The vending machine may autonomously detect that the user desires a cola and may dispense a cola and charge the amount of the cola to the user's card.

FIG. 17 shows card 1750. Card 1750 may include areas 1751-1754. Areas 1751-1754 may include multiple user interfaces (e.g., mechanical or capacitive buttons). Persons skilled in the art will appreciate that the location of areas 1751-1754 may result in a different way that a user interacts with card 1750. For example, area 1753 may be located in the proximity of the center of the bottom of card 1750 such that left and right handed users may decide to utilize area 1753 in a similar manner. Area 1751 may be located within the proximity of the center of the left side of a side of card 750 (e.g., the front side of card 750). Accordingly, a right-handed user may find it easier to rotate the card such that user views the left-side of card 750 as the top of card 750. Accordingly, indicia located on an area may be provided in an orientation that can easily be read if the card was rotated and held in a different orientation than that shown in FIG. 7 (e.g., the card is rotated such that the indicia of area 1754 is oriented properly with respect to a user of card 1750). Interfaces within an area may be aligned in a line formation or in a different formation (e.g., a directional pad formation).

A display may also be utilized as an interface. For example, a display may include a contact and an electronic ink. The electronic ink may change colors in response to, for example, a particular electrical signal being supplied to the contact. A capacitive sensor may be coupled to such a contact, however, such that a user interaction with the contact may be sensed by the capacitive sensor. Accordingly, a card may include a display that can also receive user input. Persons skilled in the art will appreciate that a display may include multiple contacts. For example, a display may include multiple 7-segment (e.g., to display digits) or 11-segment, 14-segment, or 16-segment (e.g., to display alphanumerics) regions where each segment may be coupled to a capacitive sensor.

A biometric sensor may be placed on a card or other device. Such a biometric sensor may be, for example, a fingerprint reader. Accordingly, one or more fingerprints may be stored in the memory of a card and compared to scanned fingerprints. Different fingerprints may activate the card differently (e.g., utilize a different user's payment card info).

Persons skilled in the art will appreciate that a user's payment card number (e.g., credit card or debit card number) does not have to change. A display may hide this payment card number until an appropriate unlocking code is entered into buttons of the card. Similarly, a magnetic emulator may not be provided current until the proper unlocking code is entered—thus keeping magnetic information private and not allowing undesirable readers to read a card. A security code may be displayed on the same or a different display. A button may be provided representative of an online purchase (or a user may utilize buttons to instruct the processor that an online purchase is desirable). For such an online purchase, the credit card number and the security code may be displayed—but the magnetic emulator may not be activated. In doing so, the level of security of the card is increased. Furthermore, for example, a button may be provided representative of in-store purchases (or a user may utilize buttons to instruct the processor that an in-store purchase is desirable). Accordingly, a processor may be signaled that an in-store purchase is desired. A different operation may be associated with different types of purchases (e.g., online or in-store). Accordingly, for example, magnetic emulators may be activated for an in-store environment—but not the displays. Accordingly, for example, a restaurant cashier may not be able to read the credit card number from the card, but may still be able to swipe the card. If a reader is down or a cashier requires reading particular information (e.g., a security code or credit card number information) then controls may be utilized to communicate this information. A record of the types of transactions may be stored and may be communicated in discretionary fields of data within a transmitted data track. Such record information may be utilized, for example, to further increase security and/or introduce a variety of additional functionality.

Different types of cards may be provided on a card. For example, a security ID number and a credit card number may both be provided on the same card. A button may be utilized to allow a user to provide instruction to a processor such that the processor can display (e.g., visually and/or magnetically) the desired information. For example, a user may determine to use one of a variety of payment accounts (e.g., credit and/or debit) for a purchase. An entire payment number (e.g., credit or debit) may be changed and/or hidden visually and/or magnetically. A portion of a payment card number (e.g., credit or debit) may be changed and/or hidden visually and/or magnetically.

Persons skilled in the art will appreciate that a display on the card may display a credit card number that does not change with time (or transaction or button press). Additionally, for example, a magnetic emulator (or multiple magnetic emulators) may magnetically communicate financial data that does not change with time. Such a card may reduce, for example, the effects of physical card theft and card cloning.

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipt may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICs may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICs before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICs based, for example, on time or the number of previous unlock attempts.

Figure 18:
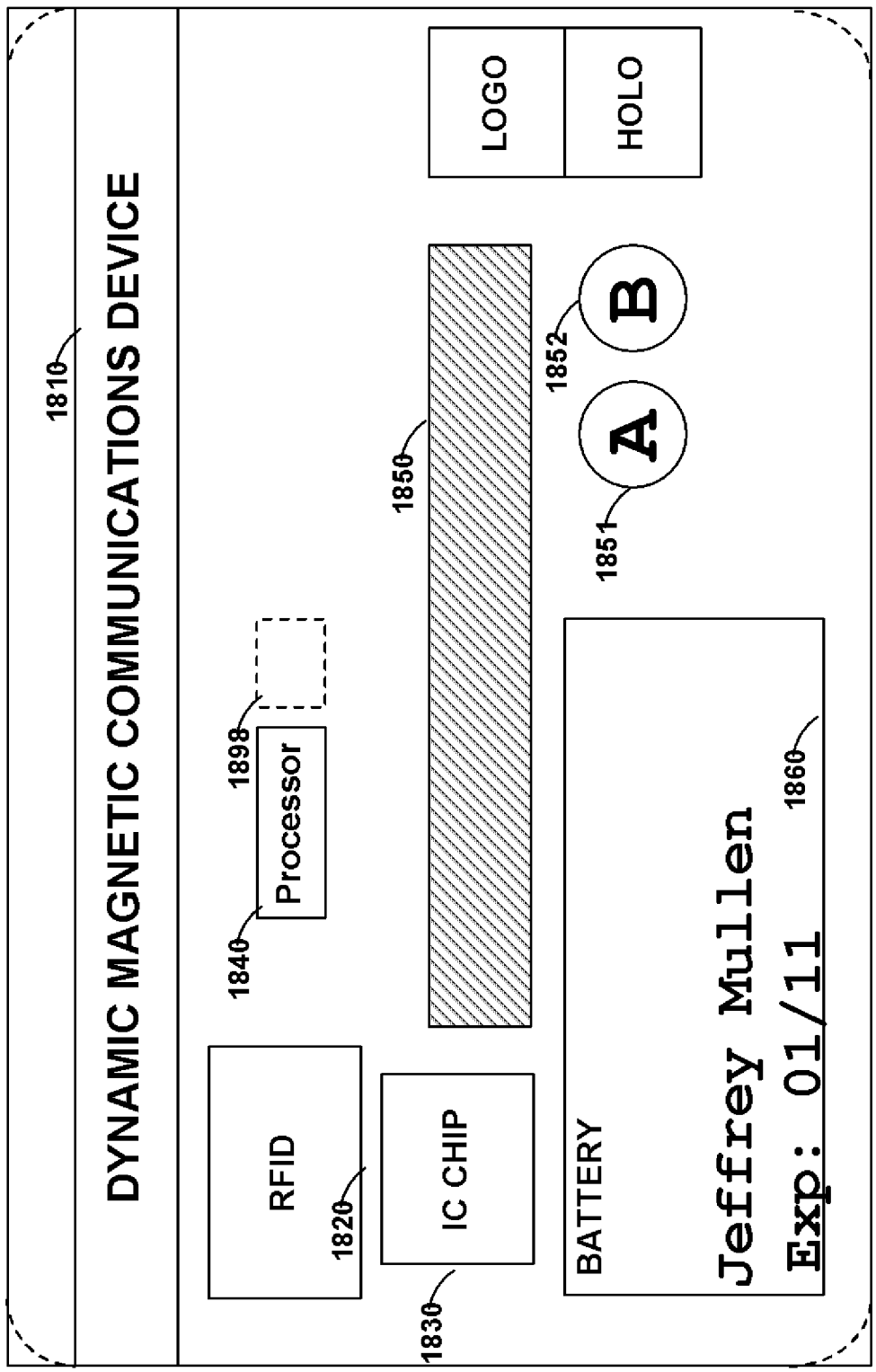
FIG. 18 is an illustration of a card constructed in accordance with the principles of the present invention.

FIG. 18 shows card 1800 that may include, for example, one or more IC chips 1830 (e.g., EMV chips), RFID antennas 1820, processors 1840, displays 1850, dynamic magnetic communications devices 1810 (e.g., magnetic encoders and/or magnetic emulators), batteries 1860, and buttons 1851 and 1852. Additional circuitry 1898 may be provided which may be, for example, one or more oscillators or emulator driving circuits. Persons skilled in the art will appreciate that button 1851 may, for example, be utilized by a user to select one encryption algorithm for a number displayed on display 1850 while button 1852 may be utilized by a user to select a different encryption algorithm. Persons skilled in the art will appreciate that the components of card 1800 may be provided on either surface of a card (e.g., a front or rear surface of the card) or inside of a card. A logo (e.g., of a card issuer) and logo may be provided on either surface of a card.

A button, such as button 1051, may be utilized, for example, to display a number. Such a number may be, for example, encrypted from a secure number based on time or use. For example, one-time use numbers (e.g., a payment number or code) may be retrieved from a list of numbers on memory each time button 1851 is pressed and displayed on display 1850. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a read-head housing may include, for example, multiple read-heads. A read-head detector may, more generally, detect a read-head housing and, in doing so, detect a read-head.

Figure 19:
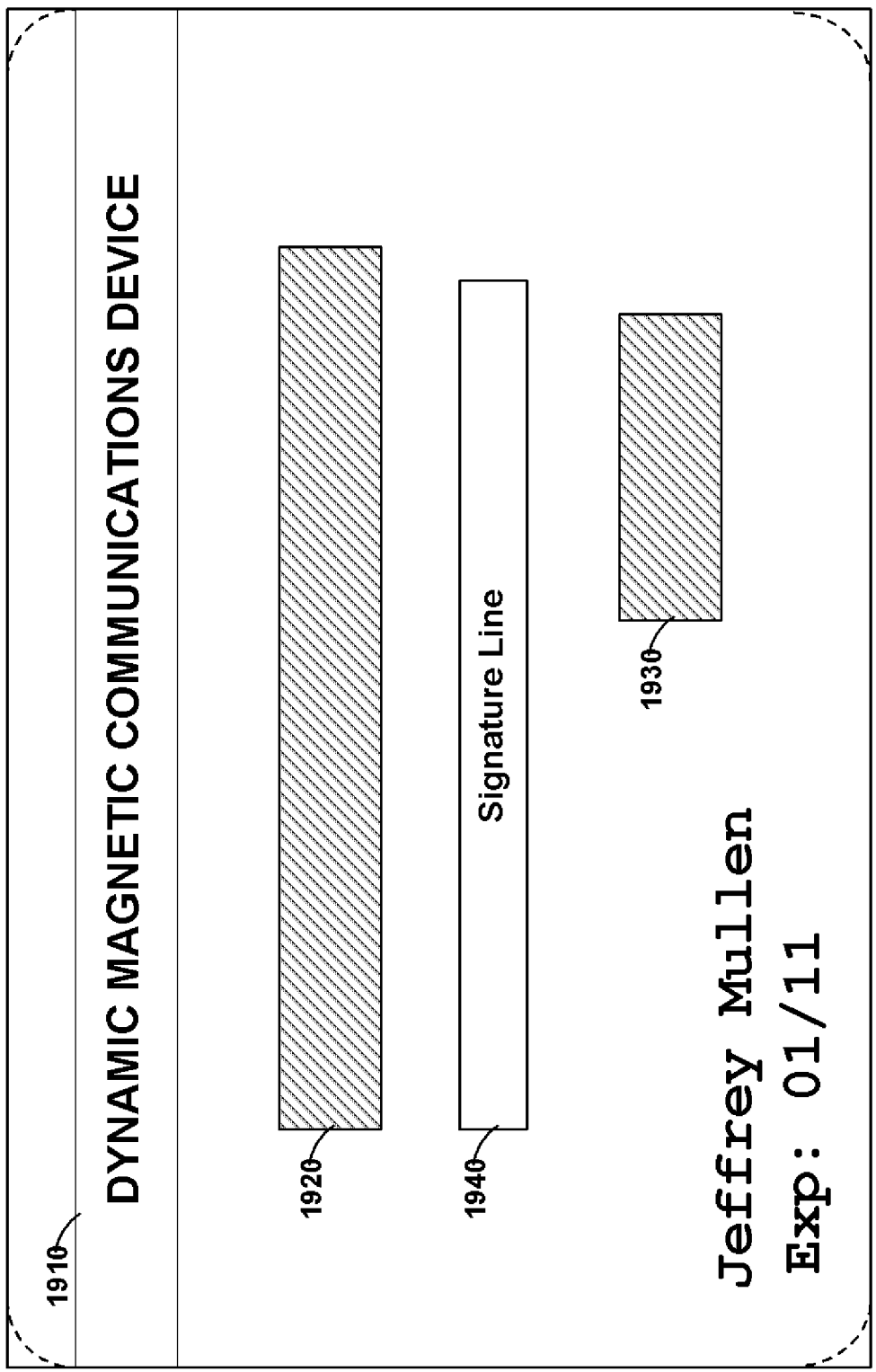
FIG. 19 is an illustration of a card constructed in accordance with the principles of the present invention.

FIG. 19 shows card 1900 that may include, for example, signature area 1940 that may include a material operable to receive marks from a pen (e.g., a signature). Card 1900 may also include, for example, displays 1920 and 1930. Display 1920 may, for example, display a payment number while display 1930 displays a security code (e.g., for online purchase authentication). Display 1920 as well as display 1930 may be utilized on the same side as, for example, dynamic magnetic communications device 1910.

Figure 20:
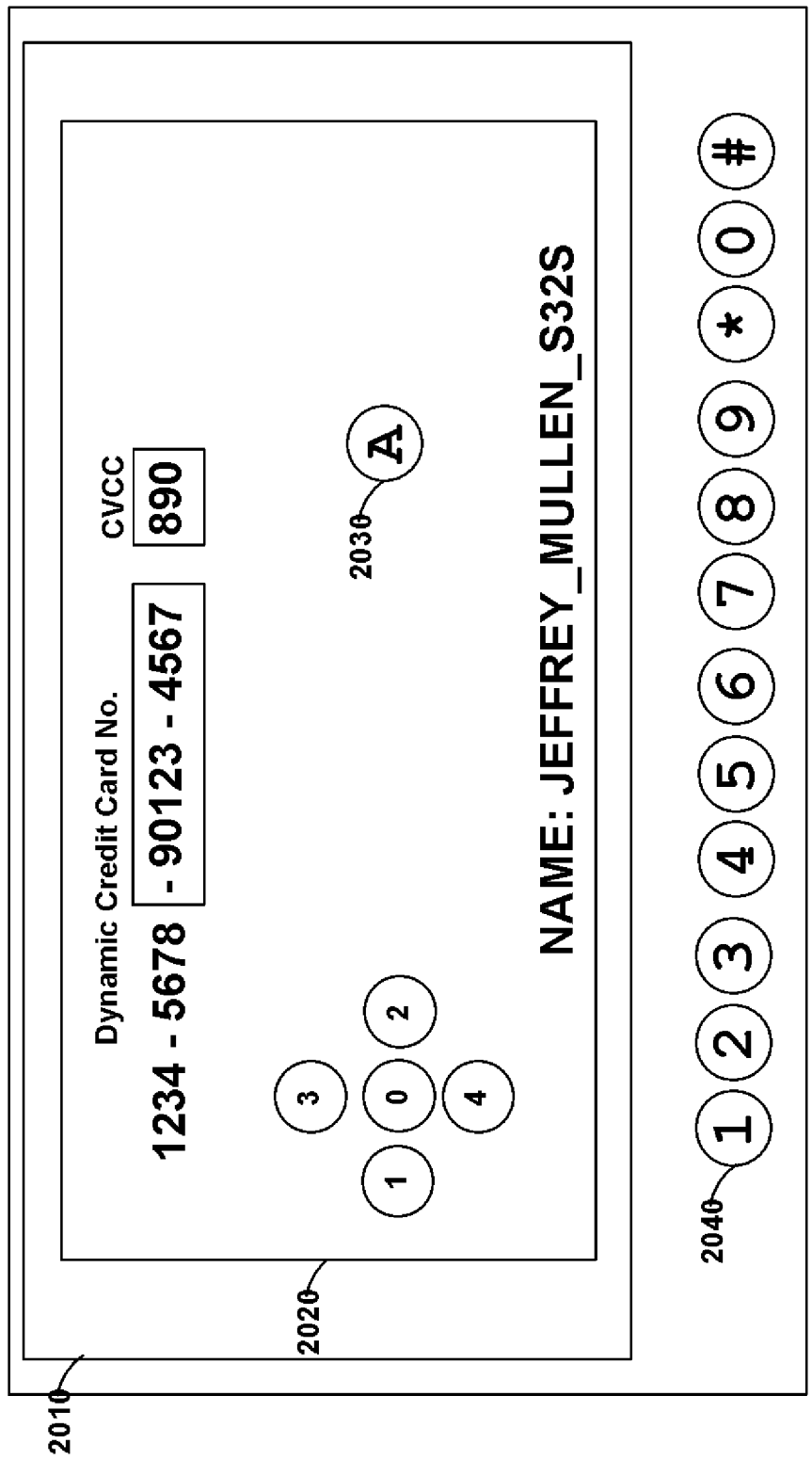
FIG. 20 is an illustration of a personal electronic device constructed in accordance with the principles of the present invention.

FIG. 20 shows personal electronic device 2000 which may be, for example, a portable telephonic device, portable media player, or any type of electronic device. Persons skilled in the art will appreciate that the functionality of a card may be provided on a personal device and displayed through a graphical user interface. Personal electronic device 2000 may include, for example, user inputs 2040 and display 2010. Virtual card 2020 may be displayed on display 2020. Display 2020 may be a touch-sensitive display such that, for example, virtual button 2030 may be provided on virtual card 2020. Persons skilled in the art will appreciate that cards may be provided as virtual cards and a user may interact with such virtual cards in order to provide a variety of functions. Personal electronic device 2000 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A system comprising:
a portable telephonic device comprising:
an array of interfaces operable to receive manual input; and
a magnetic emulator operable to communicate with a magnetic stripe reader from outside of a reading area of said magnetic stripe reader,
wherein said manual input is indicative of a personal identification code,
said device is operable to communicate a dynamic code to said magnetic stripe reader via said magnetic emulator, and
said magnetic stripe reader is operable to utilize said dynamic code to confirm a user identity.

2. The system of claim 1, wherein said device further comprises a display.

3. The system of claim 1, wherein said array of interfaces includes a first, second, third, fourth, and fifth button.

4. The system of claim 1, wherein said device further comprises an RFID.

5. The system of claim 1, wherein said device further comprises a processor,
wherein said processor controls circuitry that controls communications from said magnetic emulator.

6. The system of claim 1, wherein said device further comprises an electromagnetic field detector.

7. The system of claim 1, wherein said device further comprises a processor and an integrated circuit chip.

8. The system of claim 1, wherein said device further comprises a source of light.

9. The system of claim 1, wherein said device further comprises multiple layers of PCB.

10. The system of claim 1, wherein said device further comprises a battery.

11. The system of claim 1, wherein said device further comprises a battery, wherein said array of interfaces is an array of capacitive touch sensors of a display.

12. The system of claim 1, wherein said device further comprises a battery, a processor, and an integrated circuit chip.

13. The system of claim 1, wherein said device further comprises a first display and a second display.

14. The system of claim 1, wherein said device further comprises a second magnetic emulator.

15. The system of claim 1, wherein said device further comprises a second magnetic emulator and a third magnetic emulator.

16. The system of claim 1, wherein said device further comprises a first button and a second button, wherein said array of interfaces includes several buttons.

17. The system of claim 1, wherein said device further comprises a first source of light and a second source of light.

18. The system of claim 1, wherein said device further comprises a first display, a second display, and a third display.

19. The system of claim 1, wherein said device further comprises a first display, a second display, a third display, and a fourth display.

20. The system of claim 1, wherein said array of interfaces includes ten buttons.

21. The system of claim 1, wherein said device further comprises a first display and a second display, and said array of interfaces includes several buttons.

22. The system of claim 1, wherein said device includes a plurality of detectors.

23. The system of claim 1, wherein said magnetic emulator includes a coil.

24. The system of claim 1, wherein said device includes a light sensor.

25. The system of claim 1, wherein said device includes a plurality of light sensors.

26. The system of claim 1, wherein said device further comprises a voltage regulator.

27. The system of claim 1, wherein said device further comprises a battery and a voltage regulator.

28. The system of claim 1, further comprising an external power source,
wherein said device further comprises a voltage regulator operable to regulate power of said external power source.

29. The system of claim 1, wherein said device further comprises a first source of light, a second source of light, and a third source of light.

* * * * *